(12) United States Patent
Bachas et al.

(10) Patent No.: US 6,688,162 B2
(45) Date of Patent: Feb. 10, 2004

(54) MAGNETOELASTIC SENSOR FOR CHARACTERIZING PROPERTIES OF THIN-FILM/COATINGS

(75) Inventors: Leonidas G. Bachas, Lexington, KY (US); Gary Barrett, Manchester, NH (US); Craig A. Grimes, Boalsburg, PA (US); Dimitris Kouzoudis, Thessaloniki (GR); Stefan Schmidt, Morrisville, NC (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/067,681

(22) Filed: Oct. 20, 2001

(65) Prior Publication Data

US 2002/0166382 A1 Nov. 14, 2002

Related U.S. Application Data

(60) Provisional application No. 60/242,478, filed on Oct. 20, 2000, and provisional application No. 60/271,099, filed on Feb. 23, 2001.

(51) Int. Cl.[7] ............................................. G01N 11/16
(52) U.S. Cl. ...................... 73/64.42; 73/54.26; 73/579
(58) Field of Search ............................. 73/579, 64.42, 73/64.53, 54.25, 54.26, 61.75, 61.79, 54.41; 422/69; 435/287.2; 436/69, 151

(56) References Cited

U.S. PATENT DOCUMENTS

| | | | |
|---|---|---|---|
| 4,409,553 A | * 10/1983 | Slough et al. | 436/149 |
| 4,510,489 A | 4/1985 | Anderson, III et al. | 340/572 |
| 4,561,314 A | 12/1985 | Alley et al. | 73/862.69 |
| 4,621,503 A | 11/1986 | Woods et al. | 62/228.3 |
| 4,660,025 A | 4/1987 | Humphrey | 340/572 |
| 4,679,427 A | 7/1987 | Kanda et al. | 73/54 |
| 4,745,401 A | 5/1988 | Montean | 340/572 |
| 4,769,631 A | 9/1988 | Copeland | 340/551 |
| 4,817,430 A | 4/1989 | Benes et al. | 73/579 |
| 4,980,670 A | 12/1990 | Humphrey et al. | 340/551 |

(List continued on next page.)

OTHER PUBLICATIONS

Grimes, et al., 33–5 *IEEE Transactions on Magnetics* (Sep./ 1997) pp. 3412–3414.
Stoyanov, et al., 34–4 *IEEE Transactions on Magnetics* pp. 1315–1317 (Jul. 1998).
Barandiarán and Gutiérrez, 59 *Sensors and Actuators A* 38 (1997).
Barandiarán, et al., 5 *Int. J. of Applied Electromagnetics in Materials* 75 (1994).
Hansson, et al., 14 *Biosensors & Bioelectronics* (1999) pp. 671–682.

(List continued on next page.)

*Primary Examiner*—John E. Chapman
(74) *Attorney, Agent, or Firm*—Macheledt Bales LLP

(57) ABSTRACT

An apparatus for determining elasticity characteristics of a thin-film layer. The apparatus comprises a sensor element having a base magnetostrictive element at least one surface of which is at least partially coated with the thin-film layer. The thin-film layer may be of a variety of materials (having a synthetic and/or bio-component) in a state or form capable of being deposited, manually or otherwise, on the base element surface, such as by way of eye-dropper, melting, dripping, brushing, sputtering, spraying, etching, evaporation, dip-coating, laminating, etc. Among suitable thin-film layers for the sensor element of the invention are fluent bio-substances, thin-film deposits used in manufacturing processes, polymeric coatings, paint, an adhesive, and so on. A receiver, preferably remotely located, is used to measure a plurality of values for magneto-elastic emission intensity of the sensor element in either characterization: (a) the measure of the plurality of values is used to identify a magneto-elastic resonant frequency value for the sensor element; and (b) the measure of the plurality of successive values is done at a preselected magneto-elastic frequency.

24 Claims, 14 Drawing Sheets

U.S. PATENT DOCUMENTS

| | | | |
|---|---|---|---|
| 5,083,112 A | 1/1992 | Piotrowski | 340/572 |
| 5,130,697 A | 7/1992 | McGinn | 340/551 |
| 5,150,617 A * | 9/1992 | Schwarz et al. | 73/579 |
| 5,348,761 A | 9/1994 | Mitter et al. | 427/101 |
| 5,499,015 A | 3/1996 | Winkler et al. | 340/551 |
| 5,508,203 A | 4/1996 | Fuller et al. | 436/149 |
| 5,514,337 A | 5/1996 | Groger et al. | 422/82.08 |
| 5,538,803 A | 7/1996 | Gambino et al. | 428/694 TM |
| 5,552,778 A | 9/1996 | Schrott et al. | 340/825.34 |
| 5,554,974 A | 9/1996 | Brady et al. | 340/572 |
| 5,563,583 A | 10/1996 | Brady et al. | 340/572 |
| 5,565,847 A | 10/1996 | Gambino et al. | 340/572 |
| 5,585,772 A | 12/1996 | Joshi et al. | 335/215 |
| 5,597,534 A | 1/1997 | Kaiser | 422/82.08 |
| 5,672,812 A | 9/1997 | Meyer | 73/35.07 |
| 5,698,089 A | 12/1997 | Lewis et al. | 205/787 |
| 5,705,399 A | 1/1998 | Larue | 436/501 |
| 5,754,110 A | 5/1998 | Appalucci et al. | 340/572 |
| 5,821,129 A | 10/1998 | Grimes et al. | 436/151 |
| 5,836,203 A * | 11/1998 | Martin et al. | 73/579 |
| 5,841,350 A | 11/1998 | Appalucci et al. | 340/572 |
| 5,859,587 A | 1/1999 | Alicot et al. | 340/572 |
| 5,981,297 A | 11/1999 | Baselt | 436/514 |
| 6,018,988 A | 2/2000 | Persson | 73/54.25 |
| 6,393,921 B1 | 5/2002 | Grimes et al. | 73/728 |
| 6,397,661 B1 | 6/2002 | Grimes et al. | 73/24.06 |

OTHER PUBLICATIONS

"A Remotley Interrogatable Magnetochemical Ph Sensor" Grimes, et al., 33–5 *IEEE Transactions on Magnetics* (Sep./1997) pp. 3412–3414.

"A Remotely Interrogatable Sensor for Chemical Monitoring" Stoyanov, et al., 34–4 *IEEE Transactions on Magnetics* pp. 1315–1317 (Jul. 1998).

"Magnetoelastic Sensors Based on Soft Amorphous Magnetic Alloys" Barandiarán and Gutiérrez, 59 *Sensor and Actuators A* 38 (1997).

"Non–linear Behavior of the Magnetoelastic Resonance in Fe–rich Metallic Glasses" Barandiarán, et al., 5 *Int. J. of Applied Electromagnetics in Materials* 75 (1994).

"Surface Plasmon Resonance (SPR) Analysis of Coagulation in whole blood with application in prothrombin time assay" Hansson, et al., 14 *Biosensors & Bioelectronics* (1999) pp. 671–682.

* cited by examiner

MAGNETOELASTIC SENSOR FOR CHARACTERIZING PROPERTIES OF THIN-FILM/COATINGS

This application claims priority to two pending U.S. provisional patent applications filed by the assignee hereof: (1) serial No. 60/242,478 filed Oct. 20, 2000 and (2) serial No. 60/271,099 filed Feb. 23, 2001.

GOVERNMENTAL SUPPORT

The invention described herein was partially supported by the National Science Foundation under contracts ECS-9875104, ECS-9988598, and DGE-9870691; and by NASA under grant contract NCC5-396. Accordingly, the U.S. Government may have certain rights in this invention.

BACKGROUND OF THE INVENTION

PENDING APPLICATIONS FOR MAGNETOELASTIC SENSORS FILED BY ASSIGNEE

On Dec. 30, 1998, the assignee hereof filed a U.S. nonprovisional patent application for an applicant hereof, Dr. Craig Grimes, currently pending as Ser. No. 09/223,689 entitled "Remote Magneto-elastic Analyte, Viscosity and Temperature Sensing Apparatus and Associated Methods of Sensing". On Feb. 11, 2000 the assignee hereof filed a U.S. nonprovisional patent application for applicants hereof, Dr. Craig Grimes and Dr. Dimitris Kouzoudis, currently pending as Ser. No. 09/502,663 entitled "Magnetoelastic Sensing Apparatus and Method for Remote Pressure Query of an Environment."

FIELD OF THE INVENTION

In general, the present invention relates to telemetry techniques for direct measurement of, as well as measuring changes in, material characteristics such as mass, thickness, density, and elasticity. More particularly, the invention is directed to a new apparatus and method for remotely measuring or monitoring changes in characteristics relating to the elastic nature of a material at least partially coating a surface of a magnetostrictive element, including determining a modulus of the material's elasticity or viscous nature (e.g., Young's modulus), bulk modulus, or other such constant or coefficient expressing the degree to which a substance or material is elastic or viscous in nature), monitoring or measuring bioactive reaction responses of the material, such as coagulation reactions, blood clotting time, and so on. The sensor element is preferably remotely located (no hardwire interconnection) from an associated pick-up/receiver(s) and data processing unit(s). The thin-film/coating layer in contact with a surface of a base element may be any of a variety of inert thin-film layers or chemically-, physically-, or biologically-responsive layers (such as blood, which experiences a change in viscosity as it coagulates) for which data or material property information about the layer is desired. Among the many suitable thin-film layers for the sensor element of the invention are fluent bio-substances (such as those comprising a biologic agent or blood), thin-film deposits used in a manufacturing process, a polymeric coating, a coating of paint, and a coating of an adhesive, etc.

In one aspect of the invention, the focus is on an apparatus and technique for direct quantitative measurement of elasticity characteristic values of an unknown thin-film/coating layer (which relate to a change in mass of a bare magetoelastic element and one with any unknown coating/film in contact with a surface of the base magnetoelastic element). In another aspect of the invention, the focus is on an apparatus and technique for determining elasticity characteristics where the thin-film layer is a fluent bio-substance. In such cases, as one can appreciate, of interest in connection with a fluent substance-prior to setting, curing or drying-is its viscous nature or behavior. Fluent substances that have transformed into a solid state, are said to have 'set', 'cured', or 'dried' (e.g., coagulated blood). The bio-substance can comprise a bio-component such as a biologic agent or blood, a non-Newtonian liquid (often making direct quantitative measurement of its characteristics using standard models and testing procedures, inaccurate). Biologic agents of interest include an antibody, a biochemical catalyst (or biocatalyst) such as an enzyme, a disease-producing agent (or pathogen) a DNA component, and so on.

Although magnetoelastic materials are currently used in connection with position sensors, identification markers, and in the commercial retail arena as anti-theft or, electronic article surveillance (EAS) tags, according to the unique technique of the invention, by examining the shift in the resonant frequency of a magnetoelastic sensor element of the invention to which a given mass load (coating/film/layer) has been applied, the elastic modulus Y if the mass load can be determined where density p of the coating/film/layer is known. One important aspect of the invention relates more-particularly to techniques for measuring the viscoelastic properties of blood, including blood coagulability tests and other techniques that measure bioactive coagulation reactions. This aspect of the invention relates specifically to a new remote-query technique for measuring coagulation/clotting time of blood, or other such bioactive coagulation reaction, whereby a drop/coating of the responsive-material (e.g., blood) is placed in contact with a surface of the magnetoelastic sensor element/substrate to which a magnetic field (having an alternating magnetic field component and a DC magnetic biasing field component) is then applied.

VI. Technological History: Other Devices

Anti-theft markers/tags (electronic article surveillance, EAS, markers) generally operate by "listening"for acoustic energy emitted in response to an interrogating AC magnetic field, to sense the presence of an EAS marker. Sensormatic, Inc. distributes an EAS tag (dimensions 3.8 cm ×1.25 cm ×0.04 mm) designed to operate at a fixed frequency of 58 kHz (well beyond the audible range of human hearing). These EAS tags are embedded/incorporated into articles for retail sale. Upon exiting a store, a customer walks through a pair of field coils emitting a 58 kHz magnetic field. If a tag is still in an article being carried by the customer, the tag will likewise emit a 58 kHz electromagnetic signal that can be detected using a pickup coil, which in turn may set off an audible or visual alarm. More-recently, these tags are being placed in a box-resonator, sized slightly larger than the tag, such as the tags placed within a cavity 20 of a housing (see FIG. 2 of Winkler et al., U.S. Pat. No. 5,499,015-or simply '015).

Winkler et al. ('015) describes an electronic article surveillance (EAS) anti-theft system that operates by detecting mechanical resonances of magnetostrictive elements made of amorphous metallic glass METGLAS®2826 MB, to prevent or deter theft of merchandise from retail establishments. In response to an interrogation signal generated by energizing circuit 201, the interrogating coil 206 generates an interrogating magnetic field, which in turn excites the integrated marker portion 12 of the article of merchandise 10 into mechanical resonance. During the period that the circuit 202 is activated, and if an active marker is present in the interrogating magnetic field, such marker will generate in the receiver coil 207 a signal at the frequency of mechanical resonance of the marker. This signal is sensed by a receiver which responds to the sensed signal by generating a signal to an indicator to generate an alarm.

Anderson, III et al., U.S. Pat. No. 4,510,489-or simply '489 discloses a marker 16 (HG. 5) formed of a strip 18 of a magnetostrictive, ferromagnetic material adapted, when armed in its activated mode, to resonate mechanically at a frequency within the range of the incident magnetic field. A hard ferromagnetic element 44 disposed adjacent to the strip 18 is adapted, upon being magnetized, to magnetically bias the strip 18 and thereby arm it to resonate at that frequency. An oscillator provides an AC magnetic field within interrogation zone 12 to mechanically resonate a magnetostrictive strip 18, which has first been armed by a magnetized hard ferromagnetic element 44, upon exposure to this AC magnetic field. The sole object of Anderson, III et al. ('489) EAS marker is to detect the presence between coil units 22 and 24 (interrogation zone 12) of an "armed/activated" marker 16. In the event an activated marker 16 secured to a retail article is detected within zone 12, an alarm will sound. A deactivator system 38, electrically connected to a cash register, can be used to deactivate the marker.

Humphrey, U.S. Pat. No. 4,660,025 and, another reference, Humphrey et al., U.S. Pat. No. 4,980,670 disclose harmonic type electronic article surveillance (EAS) markers which include a thin strip or wire of magnetic material that responds to an alternating interrogation signal by generating a signal pulse that is rich in high harmonics of the interrogation signal. Schrott, et al., U.S. Pat. No. 5,552,778-or simply '778 describes a multibit bimorph magnetic ID tag for attachment to, and identification of, an object. The tag has one or more bimorphs comprised of a thin strip of a magnetostrictive material attached to a thicker bar 21 of hard magnetic material. A shipping pallet, package, or product is tagged with the bimorph for later product identification. Schrott et al. ('778) indicates that a multibit tag could be programmed to generate a binary or other suitable code. In the binary code case, a certain frequency of an array of cantilevers can be assigned a value of "zero" or "one" and, if absent, it can take the opposite value. The Schrott, et al. ('778) ID tag is limited to coded (zeros and ones) identification of the object. If, in operation, a Schrott, et al. ('778) ID tag's resonant frequency (predetermined by size/materials) is not "hit" during interrogation due to some unexpected event/external factor (such as, its resonant frequency is changed due to a temperature swing, or due to reaction of the ID tag with a surrounding fluid), no response will be detected and an incorrect output code will result, thus, destroying the Schrott, et al. ('778) ID tag's function.

Rather than working at a fixed interrogation frequency and simply checking for amplitude like the anti-theft EAS markers do to sense presence or absence of an active EAS tag on an article for purchase, the novel sensing apparatus and method of the invention looks to the frequency response of the sensor for information about the elasticity characteristics of a thin-film layer atop a magnetoelastic base element. Operating as a telemeter, elasticity characteristics of the thin-film layer can be obtained through remote query according to the invention, without direct hard-wire connection and without the need to ensure the sensor element's orientation in order to provide such information. In effect, the interrogation field to which the sensor element is exposed acts as a power source for the 'passive' sensing elements of the invention which, in turn, transmits or emits information magnetically, acoustically, and optically.

V. General Technical Background

Knowledge of the elastic properties and characteristics of materials, including stress-strain relationships, visco-elastic behavior over time (whether or not exposed to an external agent such as air or other gas), viscous nature or behavior, brittleness, bioactive reaction response, and so on, often factors heavily into engineering product and manufacturing process design and analysis. Elastic moduli are closely linked to the internal structure of solids at their atomic and microstructural levels, thus offering valuable information for materials research and development. The American Heritage Dictionary, Second College Edition, published by Houghton Mifflin Company, Boston, 1982, a revised edition of New college ed. c1976, defines a modulus as: "1. Physics. A constant or coefficient that expresses the degree to which a substance possesses some property." Measurements of the elastic moduli and their dependency on ambient conditions, for example temperature and pressure, help to evaluate material properties, material composition, and the utility for an intended application such as thin film deposition, or deposition of specific alloy composition in microcircuit device fabrication, and layering or lamination in a medical device.

In general, coagulation is the separation or precipitation from a dispersed state of suspensoid particles resulting from their growth-the separation or precipitation resulting from prolonged heating, the addition of an electrolyte, a condensation reaction between solute and solvent, and so on (an example of which is the setting of a gel). Blood, a fluent connective tissue consisting of plasma and cells, is an example of a bio-substance that coagulates. The unique nature of blood, has caused it to be characterized as a non-Newtonian fluid; thus posing a challenge for those needing to measure bioactive reactions, as well as determine clotting and coagulation time. It is important to reliably ascertain specific information about blood and other bio-components in order to perform coagulation monitoring for surgical procedures and to monitor anticoagulant therapy delivered to patients in connection with cardiac monitoring. The coagulation process of blood relies on a well known protein cascade and its interaction with blood cells and local tissue factors (see, for reference, the pages numbered 23–25 of applicants' provisional application No. 60/271,099 filed Feb. 23, 2001). Consequently the bleeding time at a surface wound will significantly differ from blood coagulation time in-vivo. Current methodologies for determining blood coagulation time rely on isolation of specific factors, thus requiring the removal of red blood cells to determine a plasma/fibrinogen isolated clotting time. Blood coagulability tests currently in use, clinically test the ability of blood to coagulate, such as to determine clot retraction time and quantification, prothrombin time, partial thromboplastin time, and platelet enumeration. For general reference concerning one such conventional technique, called Surface Plasmon Resonance (SPR), along with a discussion of the process of blood coagulation, please see the article entitled "Surface plasmon resonance (SPR) analysis of coagulation in whole blood with application in prothrombin time assay", K. M. Hansson, et al. Biosensors & Bioelectronics 14 (1999), 671–682. The apparatus and method of the invention provides a novel testing technique that can be used to determine elasticity characteristics of blood and other fluent bio-substances-of greatest interest prior to coagulation or drying being the viscous nature or behavior thereof-as a stand-alone test or used to supplement any of the testing modalities currently available to characterize blood.

SUMMARY OF THE INVENTION

It is a primary object of the invention to provide apparatus and technique for obtaining quantitative direct measurement of, as well as measuring or monitoring changes in, characteristics relating to the elastic nature of a material layer at least partially coating a surface of a base magnetostrictive element. Elasticity characteristics of interest include a modulus of elasticity (Young's modulus) value for the material, a bulk modulus value for the material, and monitoring or measuring bioactive reaction responses of the material, such as coagulation reactions, blood clotting time, and so on. No direct hard-wire connection to an interrogation field generating coil or to a magneto-elastic emission receiving coil, is needed; but rather the receiver unit is remotely located for the sensing.

As can be appreciated, the innovative compact apparatus and method use a base magnetostrictive element to which a thin-film layer has been added/deposited/layered as contemplated and described herein, accommodate a variety of measurement and monitoring techniques and structural alternatives, including but not limited to the following identified features—all within the spirit and scope of design goals contemplated hereby. Advantages of providing the new elasticity sensing apparatus and associated method, include without limitation:

(a) The invention can be used for one-time disposable operation (e.g., in the form of a kit) or continuous monitoring of a particular thin-film/coating/layer to observe characteristics of the thin-film as it reacts to some agent over time (e.g., observing blood as it coagulates to create a coagulation response curve or determine a blood clotting time);

(b) Versatility—The invention can be used to measure physical properties of a wide range of thin-films/coatings in connection with biomedical applications (such as within medical test samples), manufacturing operations, material science research tool applications, and so on. In the context of a disposable kit or tool for monitoring a bio-substance having a component such as a biologic agent (biocatalyst, pathogen, DNA component, etc.) or blood, the apparatus provides a portable point-of-care diagnostic tool for real-time, immediate as well as ongoing monitoring of an anticoagulation, or other medicine, therapy-such as might be needed during, prior to, or post-surgery or treatment. By offering nearly-instantaneous results, one eliminates the need for long-term storage of blood and anticoagulant treatment prior to performing the characterization of the blood (esp. since storage and such treatment may cause erroneous results).

(c) Simplicity of use—The new sensing apparatus can produce measurement results with relative ease. Monitoring and measurement of a variety of elasticity characteristics may be performed without requiring sophisticated equipment and complicated procedures. For example, real-time monitoring of the deposit of a layer(s) in a wafer or microchip fabrication process can take place by positioning sensor elements within a vacuum chamber/clean room and remotely measuring emissions from outside the chamber, while the manufacturing process is taking place. Further, the simplicity of design allows for ready incorporation of a sensing element of the invention into self-diagnostic kits (such as is presently available for glucose monitoring of diabetic patients). The relatively small amount of blood necessary for characterization utilizing the sensing system of the invention makes collection from an unsedated, conscious patient less troublesome. Present monitoring practices require the removal of relatively large blood samples (2–10 ml) and extensive sample preparation prior to titration analysis resulting in a prolonged testing regime, which can require several hours for result generation. Use of a sensing kit incorporating a sensing element of the invention significantly reduces testing time, blood volume removed (patient distress) while still providing comparative results.

(d) Speed of results—The speed with which blood, or other sample-fluent bio-substance, may be characterized using the sensing element of the invention allows it to be used in connection with surgical procedures where constant, real-time monitoring (sampling and ready results) of blood coagulation is critical. Certain medication therapy requires, at times, nearly instantaneous evaluation/results. For example, use of anticoagulation therapy is extensive during certain cardiac surgical procedures; and whether done as an in-patient, or out-patient basis, speedy results are often imperative.

(e) Structural design—The thin-film layer of interest adhered to the magnetostrictive base may be shaped or applied in a manner that optimizes the speed at which an activity, reaction, or response occurs over time to an external agent (e.g., air or humidity), allowing the sensor apparatus to provide useful information at a faster rate. The sensor elements can be formed into many different shapes of various sizes; for example, the sensor elements may be fabricated on a micro-circuit scale for use where space is extremely limited such as within small-sized sealed packaging or medical test samples (e.g., a test tube), or on a larger scale.

(f) Several sensor elements may be incorporated into an array to provide a 'package' of various information relating to elasticity characteristics of the thin-film layer by sampling simultaneously or sequentially, each of several different base elements having various different thin-film layers.

(g) Receiving unit design flexibility-One unit may be built with the capacity to receive acoustic emissions (elastic waves with a frequency up into the gigahertz, GHz, range) as well as electromagnetic emissions emanating from the sensor element, or separate acoustic wave and electromagnetic wave receiving units may be used.

(h) Apparatus design simplicity—Reducing the number and size of components required to accomplish measurements/monitoring of elasticity characteristics reduces overall fabrication costs, making kits economically feasible, and adds to ease of operation.

Briefly described, once again, the invention includes an apparatus for determining elasticity characteristics of a thin-film layer. By way of example only, occasional reference will be made, here, to FIG. 17 where certain core, unique features of method 100 are labeled. The apparatus comprises a sensor element having a base magnetostrictive element at least one surface of which is at least partially coated with the thin-film layer. The thin-film layer may be of a wide variety of materials (having a synthetic and/or bio-component) in a state or form capable of being deposited, whether manually or otherwise layered, on the base element surface, such as by way of eye-dropper, melting, dripping, brushing, sputtering, spraying, etching, evaporation, dip-coating, laminating, and so on. Among the many suitable thin-film layers for the sensor element of the invention are fluent bio-substances (such as those comprising a biologic agent or blood), thin-film deposits used in a manufacturing process, a polymeric coating, a coating of paint, and a coating of an adhesive, and so on.

There are many further distinguishing features of the apparatus and method of the invention. A receiver, preferably remotely located from the sensor element, is used to measure a plurality of values for magneto-elastic emission intensity of the sensor element (box 104): (a) in one characterization, the measure of the plurality of values is used to identify a magneto-elastic resonant frequency value for the sensor element (box/ 106); and (b) in another characterization, the measure of the plurality of successive values is done at a preselected magneto-elastic frequency, $f_x$ (box 107) where, for example, (the magneto-elastic resonant frequency, $f_o$, of the sensor element may be preselected as $f_x$, or some other selected frequency may be selected). In characterization (a), using a value for density of the thin-film layer and a value for mass of the base magnetostrictive element and the magneto-elastic resonant frequency value so identified, at least one of the elasticity characteristics for the thin-film layer can be determined (box 108). In characterization (b), an elasticity response profile for the thin-film layer (here, a bio-substance) can be produced by using the values for emission intensity measured (box 109). Elasticity characteristics that may be determined according to the invention include any modulus/value (boxes 108, 110, 112), as well as any elasticity response profile (box 109), that provides information as to the elasticity or general elastic nature of the thin-film layer material, including among other things: the modulus of elasticity, Young's or other modulus, $Y_c$, or bulk modulus; any bioactive reaction response curve, such as a coagulation reaction curve for the bio-substance; and in the case of blood, a blood clotting (or coagulation) time. For example, a coagulation reaction curve (or other bioactive reaction response curve) may be produced according to the invention by plotting, over a selected response-time interval, a plurality of successive voltage values respectively associated with the plurality of successive values for magneto-elastic emission intensity measured.

A value for the modulus of elasticity, $Y_c$, of the thin-film layer can be directly obtained using an apparatus and method of the invention according to the expression:

$$Y_c = \rho_c \cdot 4L^2 f_0^2 \cdot \frac{\sum_{i=1}^{N}\left(\left(\frac{f_i'}{f_0}\right)^2 - \frac{m_0}{m_i'}\right)\left(1 - \frac{m_0}{m_i'}\right)}{\sum_{i=1}^{N}\left(1 - \frac{m_0}{m_i'}\right)^2} \quad \text{Eqn. 1}$$

Eqn. 1 represents the general case where several thin-film layers from 1, 2, ... N are applied consecutively (i =1,2 ...N) to a base magnetostrictive element. As is readily apparent, Eqn. 1 is simplified where only one thin-film layer is deposited, thus, i =1 and no summation is necessary. Here, $m_0$ is the initial mass of the base element (without a thin-film layer) and $f_0$ is the base element's resonant frequency measured with no thin-film layer. Once the base element is at least partially coated with one or more thin-film layers, a new mass $m_i'$ and resonant frequency $f_i'$ of the sensor element measured after each coating/layer is applied, are used in the summation of Eqn. 1. Thus, where a single layer is applied to the base element i =1 and no summation is necessary, and one can readily appreciate that Eqn. 1 simply reduces to the following expression for modulus value, $Y_c$:

$$Y_c = \rho_c \cdot 4L^2 f_0^2 \cdot \frac{\left(\left(\frac{f'}{f_0}\right)^2 - \frac{m_0}{m'}\right)}{\left(1 - \frac{m_0}{m'}\right)^2}$$

wherein $p_c$ denotes density of the thin-film layer, L denotes length of the base element, $m_0$ denotes a mass of the base element (i.e., without a thin-film layer yet applied), $f_0$ represents the resonant frequency of the magnetostrictive element measured with no thin-film layer yet applied, m' denotes a mass of the sensor element (i.e., including the base element coated with thin-film layer), and f' denotes a resonant frequency of the base element measured with the thin-film layer applied.

The biologic agent and other components in the thin-film layer are preferably compatible so that any reaction or activity of the thin-film layer intended for monitoring according to the invention, will take place within the time interval during which values for magneto-elastic emission intensity of the sensor element are measured. The biologic agent can include is antibody, a biochemical catalyst, or biocatalyst, such as an enzyme, a disease-producing agent, or pathogen, a DNA component, and so on, included at as a component of the thin-film layer and for which information and/or monitoring of identified elasticity characteristics is desired. The base magnetostrictive element may be made of an alloy of an element selected from many elements known to have mangetostrictive properties such as iron, cobalt, samarium, yttrium, gadolinium, terbium, and dysprosium. The base element may take on a wide variety of shapes having at least one surface on which the thin-film layer can be deposited or layered, including elongated ribbon shapes, rectangular-elongated (whereby a length, l, of the sensor element is at least twice its width, w), circular, oval, polygonal, etc.; those shapes that allow sufficient vibration of the sensor element and remote receipt of its emissions, are preferred. Depending upon the means of depositing employed, the thin-film layer can readily be applied so that its thickness, $t_{tf}$, is less than a thickness, $t_{mag}$, of the base magnetoelastic element (such as could be the case if the thin-film layer is sputtered onto the base element according to microcircuit fabrication techniques).

A sensor element of the invention can emit different types (generally EM waves are lumped by frequency ranges over the EM Frequency Spectrum) of measurable emissions when exposed to a time-varying interrogation magnetic field. The interrogation field may be generated continuously over time (such as over a selected time interval) or the interrogation field may be generated in the form of a pulse, after which the measurement of emission intensity is made. Depending upon the receiver, the emissions measured may be acoustic, electromagnetic, or optical in nature. Electromagnetic emissions are received by an EM pick-up coil. If acoustic emissions from a sensor element are targeted, an electroacoustic receiving device containing a transducer for operation over a range of frequencies from 1 KHz to 1 GHz may be used. Optical waves are received by an optical receiving device.

Associated with the apparatus disclosed hereby, the invention also covers a method for determining elasticity characteristics of a thin-film layer at least partially coating a surface of a base magnetostrictive element. In a first characterization of the method of the invention, steps include: applying a time-varying interrogation magnetic field to a sensor element comprising the base magnetostrictive element and thin-film layer, operatively arranged to vibrate in response to the interrogation magnetic field (box 102, FIG. 17); remotely measuring a plurality of values for magneto-elastic emission intensity of the sensor element to identify a magneto-elastic resonant frequency value therefor (box 104, FIG. 17); and using a value for density of the thin-film layer, a value for mass of the base magnetostrictive elements and and magneto-elastic resonant frequency value, determining at least one of the elasticity characteristics (box 108, FIG. 17).

In a second characterization of the method of the invention, once a time-varying interrogation magnetic field is applied to a sensor element comprising the base magnetostrictive element and thin-film layer of a fluent bio-substance (box 102, FIG. 17), a plurality of successive values for magneto-elastic emission intensity of the sensor element at a preselected magneto-elastic frequency are remotely measured (box 104, FIG. 17). Using the values for emission intensity measured over a selected response-time interval, an elasticity response profile for the bio-substance can be produced (box 109, FIG. 17. The elasticity response profile can comprise a coagulation reaction curve, or other bioactive reaction response curve, for the bio-substance. Other information relating to elasticity characteristics of the thin-film fluent bio-substance layer can be obtained according to the invention, including clotting/coagulation time, enzyme reaction time, pathogen growth, and so on (box 112, FIG. 17).

BRIEF DESCRIPTION OF THE DRAWINGS

For purposes of illustrating the innovative nature plus the flexibility of design and versatility of the preferred apparatus and technique disclosed hereby, the invention will be better appreciated by reviewing any accompanying drawings (in which like numerals, if included, designate like parts). One can appreciate the many features that distinguish the instant invention from known devices and techniques. The have been included to communicate the features of the innovative structure and method of the invention by way of example, only, and are in no way intended to unduly limit the disclosure hereof.

DETAILED DESCRIPTION OF THE PREFERRED EMBODIMENTS

Figure 1A:
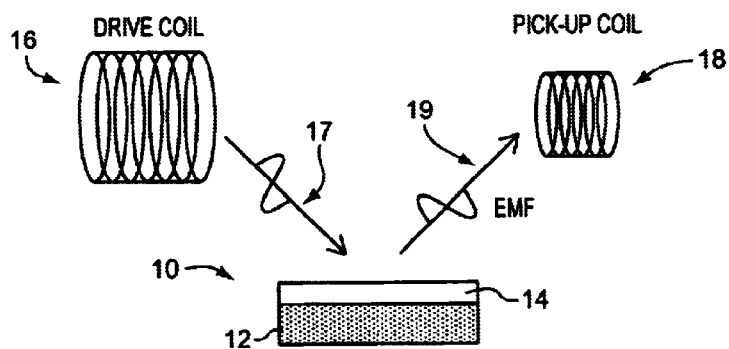
FIG. 1A schematically depicts components of an apparatus and method of the invention for remote query of a thin-film layer or coating atop a base magnetostrictive element.
Figure 1B:
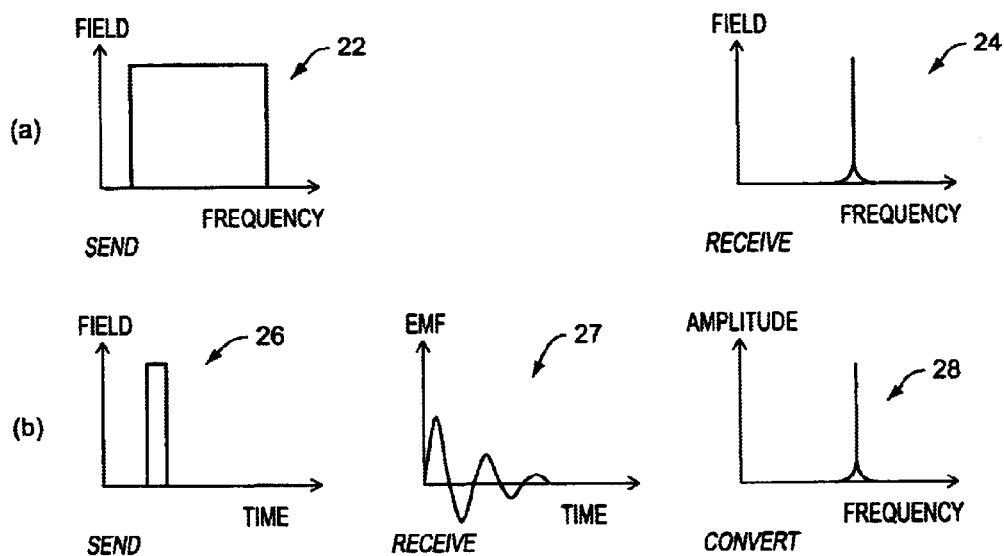
FIG. 1B graphically depicts interrogation field transmissions from a drive coil (SEND) in both the frequency domain (a) and in the time-domain (b) whereby the emissions received are accordingly converted to frequency domain to identify a resonant frequency value (RECEIVE).

FIG. 1A schematically depicts components of an apparatus and method of the invention for remote query of a thin-film layer or coating 14 atop a base magnetostrictive element 12. A time-varying magnetic field 17 is applied to sensor element 10, with a layer/coating 14 of interest having been deposited onto a surface of the base 14, by way of a suitable drive coil 16 such that emissions 19 from the sensor element can be picked-up by a suitable pick-up coil 18. Two useful ways to measure the frequency spectrum include: frequency domain measurement and the time domain measurement. In the frequency domain measurement, the sensing element's vibration is excited by an alternating magnetic field of a monochromatic frequency. The amplitude of the sensor response is then registered while sweeping ('listening') over a range of frequencies that includes the resonance frequency of the sensor element. Finding the maximum amplitude of the sensor response leads to the characteristic resonant frequency. FIG. 1B graphically depicts interrogation field transmissions from a drive coil (SEND) in both the frequency domain 22 and in the time-domain 26 (an impulse of, say, 200 A/m and 8 $\mu s$ in duration). The transient response (emissions) captured 27 is converted to frequency domain 28 using a FFT to identify a resonant frequency.

As it is well known, electric and magnetic fields are fundamentally fields of force that originate from electric charges. Whether a force field may be termed electric, magnetic, or electromagnetic hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant velocities relative to the observation point. Accelerated motions, on the other hand, produce both time-varying electric and magnetic fields termed electromagnetic fields. For general reference see the textbook, Engineering Electromagnetic Fields and Waves, Carl T. A. Johnk, John Wiley & Sons, $2^{nd}$ Edition (1988). One well known wide use or these principles or electromagnetism is me transformer: An assembly having a ferromagnetic core around which a primary coil carrying a time-varying current is wound and a secondary coil is wound—see attached APPENDIX B for reference.

Magnetic material/substances exhibit magnetic and elastic phenomena. Magnetic interaction depend of the distance of the interacting particles and consequently magnetic and mechanic effected interact. In ferromagnetic materials, magnetostriction is observed: The dimensions and elastic properties of magnetic materials often depend on the state of magnetization (direct magnetoelastic effect). Materials that possess both effects, especially magnetically soft ferromagnetic materials (i.e. materials having a low coercive forces), are commonly referred to as magnetoelastic materials.

Simply stated, "magnetostriction" is the phenomena whereby a material will change shape (dimensions) in the presence of an external magnetic field. This effect is brought about by the reordering of the magnetic dipoles within the material. Since the atoms in a magnetostrictive material are not, for all practical purposes, perfectly spherical (they're shaped more like tiny ellipsoids) the reordering of the dipoles causes an elongation (or contraction depending on the mode of reorientation) of the lattice which leads to a macroscopic shape change in the material. Note that there is a "reverse magnetostrictive effect", also known as the Villari effect: When an external stress is applied to a magnetostrictive material, a strain develops within the material which induces a surrounding magnetic field. Known magnetostrictive materials include alloys of iron (Fe), cobalt (Co), samarium (Sm), yttrium (Y), gadolinium (Gd), terbium (TB), and dysprosium (Dy).

Magnetostrictive magnetoelastic materials efficiently convert magnetic energy to mechanical elastic energy, and vice versa. Amorphous metallic glassy ribbons or wires posses a low magnetocrystalline anisotropy field and low intrinsic stress, allowing efficient magnetoelastic energy conversion; these alloys are manufactured in a melt quenching process. There are many magnetostrictive materials currently available that may be used to construct a sensing element of the invention. Two suitable amorphous metallic (glassy) alloys are commercially available under the brand names of METGLAS® (a registered trademark of Honeywell International, Inc.) and SENSORVAC® (a registered trademark of Vaccumschmelze (VAC) Corporation) alloys. The amorphous cobalt based alloy known commercially as METGLAS® 2826 MB (distributed by Allied Signal, Inc. in New Jersey) is vacuum annealed in the presence of a DC magnetic field to enhance magnetostriction. Another available magnetostrictive amorphous Co-based magnetically soft alloy is known commercially as ATALANTE® film, distributed by Innovative Sputtering Technology N.V. of Karreweg, Belgium (this film is used throughout Europe in anti-theft retail item markers). The composition, and any tempering done, of the material chosen for construction of the magnetostrictive sensing element will affect operating characteristics of a sensor structure built therewith. It is preferable to choose a magnetostrictive material that remains relatively stable (i.e., its material properties do not change a significant amount) over the expected range of operating temperatures.

When a sample of magnetoelastic material is exposed to an alternating magnetic field, it starts to vibrate. This external time-varying magnetic field can be a time-harmonic signal or a non-uniform field pulse (or several such pulses transmitted randomly or periodically). If furthermore a steady DC magnetic field is superimposed to the comparatively small AC magnetic field, these vibrations occur in a harmonic fashion, leading to the excitation of harmonic acoustic waves inside the sample. The mechanical oscillations cause a magnetic flux change in the material due to the inverse magnetoelastic effect. These flux changes, in unison with the mechanical vibrations, can be detected in a set of EM emission pick-up coils. The vibrations of the sample are largest if the frequency of the exciting field coincides with the characteristic acoustic resonant frequency of the sample. Thus, the magnetoelastic resonance frequency detectable by an EM pick-up coil coincides with the frequency of the acoustic resonance. And, sensor element emissions can be detected acoustically, for example by a remote microphone/hydrophone or a piezoelectric crystal, by detecting the acoustic wave generated from the mechanical vibrations of the sensor. A relative-maximum response of the emissions remotely measured is identified to determine the sensing element's characteristic resonant frequency. The emissions from a sensing element of the invention can also be monitored optically whereby amplitude modulation of a laser beam reflected from the sensor surface is detected. Signal processing of the sensor elements can take place in the frequency-domain or in the time-domain using a field-pulse excitation.

Figure 2:
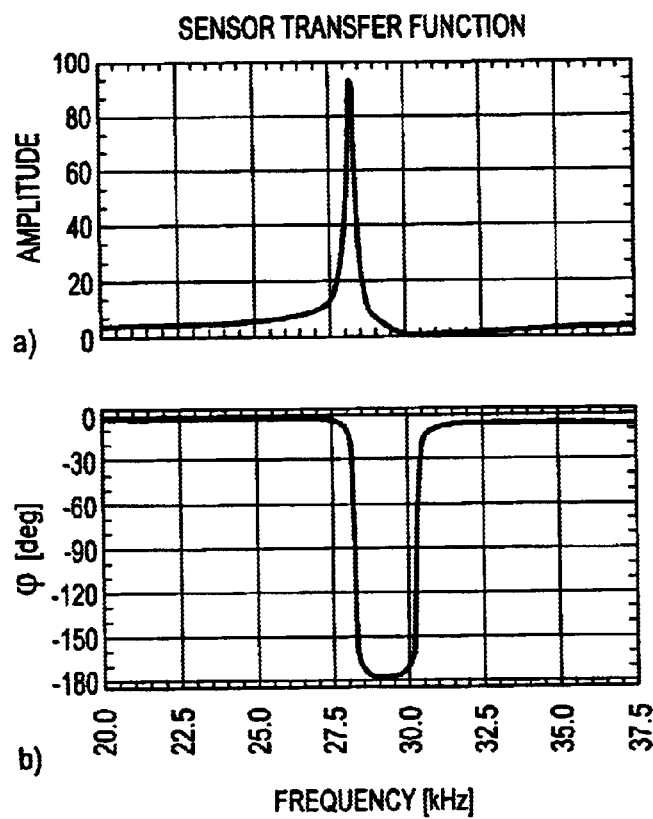
FIG. 2 graphically depicts the transfer function measured for a sensor element using a pick-up coil such as is depicted in FIG. 1A: the graph (a) shows amplitude against frequency and graph (b) illustrates the phase relationship with frequency.

FIG. 2 graphically depicts the transfer function measured for a sensor element using a pick-up coil such as is depicted in FIG. 1A: the graph (a) shows amplitude against frequency and graph (b) illustrates the phase relationship with frequency.

Figure 3:
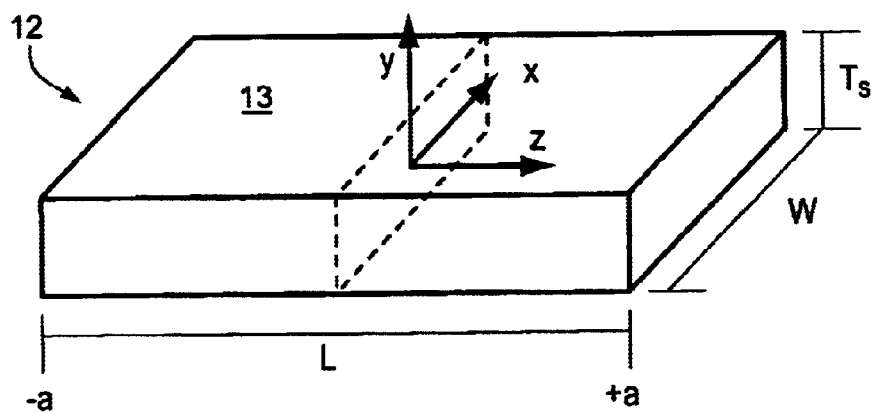
FIG. 3 schematically depicts geometry of a base magetoelastic ribbon-shaped element with dimensions labeled for reference: width w, thickness Ts, and length L, where L=2a. The element is elongated and with w≈a, preferably 2w≦L.
Figure 4:
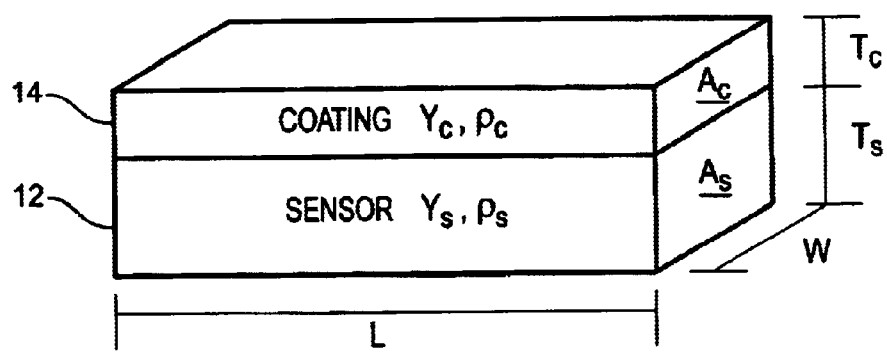
FIG. 4 schematically depicts geometry of the base element of FIG. 3, having a Young's modulus identified as $Y_s$ and density $\rho_s$, to which a coating or thin-film layer has been added having a Young's modulus identified as $Y_c$ and density $\rho_c$.
Figure 5:
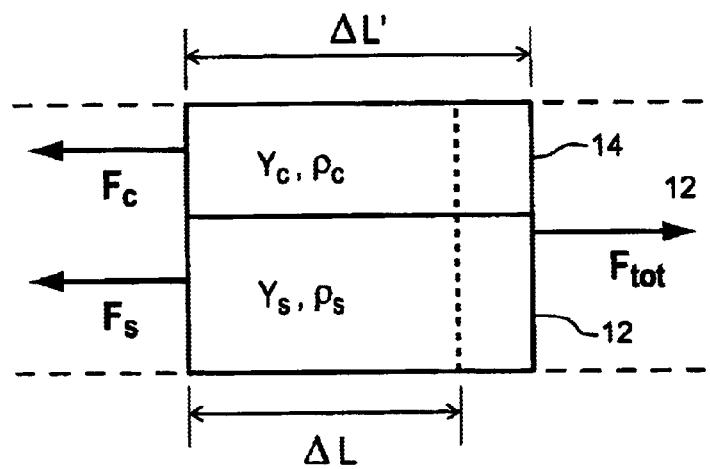
FIG. 5 schematically depicts geometry of an infinitesimal section (for purposes of derivations made, below, in connection with the invention) of the sensor element of the invention represented in FIG. 4 comprising the base element with coating/thin-film layer.

FIG. 3 schematically depicts geometry of a base magetoelastic ribbon-shaped element with dimensions labeled for reference: width w, thickness T., and length L, where L=2a. The element is elongated and with w a, preferably $2w \leq L$. FIG. 4 schematically depicts geometry of the base element of FIG. 3, having a Young's modulus identified as $Y_s$ and density $\rho_s$, to which a coating or thin-film layer has been added having a Young's modulus identified as $Y_c$ and density $\rho_c$. In addition to labeling cross-sectional area of the base element, $A_s$, and cross-sectional area for the coating/layer, $A_c$, total thickness of the sensor element is $T_c+T_s$. FIG. 5 schematically depicts geometry of an infinitesimal section $\Delta L$ and $\Delta L'$ (for purposes of derivations made, below) of the sensor element of the invention represented in FIG. 4 comprising the base element with coating/thin-film layer.

Referring to FIGS. 3, 4 and 5 collectively: The element 12 has a surface 13 on which the thin-film layer/coating has been deposited in a mamier corresponding and compatible with the type of material/substance of the layer and the type of information desired from the test/monitoring or measurement. The thin-film layer may be of a wide variety of materials (having a synthetic and/or bio-component) in a state or form capable of being deposited, whether manually or otherwise layered, on the base element surface, such as by way of an eye-dropper, melting, dripping, brushing, sputtering, spraying, etching, evaporation, dip-coating, laminating, and so on. Among the many suitable thin-film layers for the sensor element of the invention are fluent bio-substances (such as those comprising a biologic agent or blood), thin-film deposits used in a manufacturing process, a polymeric coating, a coating of paint, and a coating of an adhesive, etc.

As mentioned, the magneto-elastic emission from a sensor element of the invention may be an acoustic emission, an electromagnetic emission, or other detectable wave type emitted by the sensor. The type of receiver used (such as an electroacoustic device containing a transducer or an electromagnetic pick-up coil) will depend upon the type of magneto-elastic emission intended for measurement. If EM emission intensity is to be measured by the receiver, one may choose to perform such measurement after the time-varying magnetic interrogation field has been turned off (e.g., a magnetic field pulse). Ferromagnetic materials are inherently magnetostrictive. Suitable alloys for use as the base element 12, known for their magnetostrictive properties include: iron (Fe), cobalt (Co), samarium (Sm), yttrium (Y), gadolinium (Gd), terbium (TB), and dysprosium (Dy).

A piece of ferromagnetic material exposed to a time-varying (sinusoidal) magnetic field will in turn emit acoustic and thermal energy due to the changes in size and viscous flexing of the material. An acoustic wave is defined as an elastic wave with a frequency that may extend into the gigahertz (GHz) range. Acoustic transmission is that transfer of energy in the form of regular mechanical vibration through a gaseous, liquid, or solid medium. Acoustic emission is the phenomenon of transient elastic-wave generation due to a rapid release of strain energy caused by a structural alteration in a solid material (stress-wave emission). An ultrasonic wave is one that has a frequency above about 20 KHz Oust above human hearing). Additionally, exposure of a time-varying magnetic field will induce a time-varying current in a ferromagnetic sample such that it will emit EM energy. A magnetostrictive base element placed within an environment generally reacts to temperature variations as follows: A large swing or change in temperature of the environment will change the Young's modulus of elasticity of an element, resulting in a corresponding change in the resonant frequency of the base element. It is preferred that an alloy be chosen for the invention having material properties that remain generally unchanged over a selected range of operating temperatures.

Resonance Model for Sensor Element

For an elongated shape magenetostrictive element (ribbon or wire-shaped, or other such elongated shape with a length greater than cross-sectional area, both ends free or supported), the first longitudinal resonant frequency can be approximated by the general expression below:

$$\omega_r = 2\pi f_r = \frac{\pi}{l}\sqrt{\frac{E(H,T)}{\rho}} \qquad \text{Eqn. 2}$$

where $f_r$ denotes the resonant frequency of the magnetoelastic element, l is the length of the element, E is Young's modulus of elasticity, and $\rho$ is material density. Higher harmonic frequencies can be determined by multiplying the right-hand side of Eqn. 2 by successive integer values, i.e. n=1, 2, 3, 4, . . . . As noted, Young's modulus E of a magnetostrictive piece of material is dependent upon temperature T and applied static magnetic field H.

The frequency of the magnetoelastic resonance coincides with the resonance of the acoustic vibration. Thus, the resonance of the sensor ribbon can be modeled as the mechanical resonance of a thin longitudinally vibrating bar. According to the fundamentals of acoustic theory, a bar fixed in its center and vibrating longitudinally with free ends has resonant frequencies:

$$f_n = (2n+1) \cdot \sqrt{\frac{Y}{\rho}} \cdot \frac{1}{2L} \qquad \text{Eqn. 3}$$

where Y is Young's Modulus of elasticity, $\rho$ is the density, and L is the length of the sensor ribbon. The index n (0,1,2 . . . ) gives the order of the higher harmonics. The group velocity of a longitudinally traveling wave is:

$$v_L = \sqrt{\frac{Y}{\rho}} \qquad \text{Eqn. 4}$$

If the sensor is coated with a layer of an elastic material as shown in FIG. 4, its resonant frequency will change unless $V_{Lc}=V_{Ls}$. Considering a section of the sensor ribbon as shown in FIG. 5, and taking a coating where $T_c \ll T_s$, under application of a force $F_{tot}$ the coating 14 and the base element 12 material have a common tensile strain $\epsilon$. Having $F_{tot}$ as the superposition of the tensile force in the coating $F_c$ and in the sensor $F_s$ and $\epsilon = \epsilon_c \times \epsilon_s$, we can calculate the effective Young's Modulus of elasticity of the sensor-coating-compound as:

$$Y_{\mathit{eff}} = \alpha_c \cdot Y_c + \alpha_s \cdot Y_s \qquad \text{Eqn. 5}$$

where $\alpha_c$ and $\alpha_s$ are the fractional cross section $$\left(\frac{A}{A_{total}} = \alpha\right)$$

of the coating and sensor respectively. The effective density of a coated sensor is given when relating the total mass $m' = m_c + m_0$ to the separate masses of coating $m_c$ and sensor $m_0$ resulting in:

$$\rho_{\mathit{eff}} = \alpha_c \cdot \rho_c + \alpha_s \cdot \rho_s \qquad \text{Eqn. 6}$$

From Eqn. (3), we find the fundamental resonant frequency of an uncoated sensor as:

$$f_0 = \sqrt{\frac{Y_s}{\rho_s}} \cdot \frac{1}{2L} \qquad \text{Eqn. 7}$$

and the fundamental resonant frequency of a coated sensor:

$$f' = \sqrt{\frac{Y_{\mathit{eff}}}{\rho_{\mathit{eff}}}} \cdot \frac{1}{2L} \qquad \text{Eqn. 8}$$

The ratio of the resonant frequencies before and after a coating is applied can be written as:

$$\frac{f'}{f_0} = \sqrt{\frac{\alpha_c \cdot Y_c + \alpha_s \cdot Y_s}{\alpha_c \cdot \rho_c + \alpha_s \cdot \rho_s}} \cdot \sqrt{\frac{\rho_s}{Y_s}} = \sqrt{\frac{1 + \alpha_c \cdot \left(\frac{Y_c}{Y_s} - 1\right)}{1 + \alpha_c \cdot \left(\frac{\rho_c}{\rho_s} - 1\right)}} \qquad \text{Eqn. 9}$$

The same written in terms of the applied mass load yields:

$$\frac{f'}{f_0} = \sqrt{(1 - \beta^2)\frac{m_0}{m'} + \beta^2} = \sqrt{\frac{m_0}{m'} + \beta^2\left(1 - \frac{m_0}{m'}\right)} \qquad \text{Eqn. 10}$$

with $\beta$ being the parameter determining the slope and sign of the frequency change upon an applied coating with:

$$\beta = \frac{\sqrt{\frac{Y_c}{\rho_c}}}{\sqrt{\frac{Y_s}{\rho_s}}} = \frac{v_{Lc}}{v_{Ls}} \qquad \text{Eqn. 11}$$

Looking at Eqn. 10 one can see that the sensitivity (i.e., the change of the resonant frequency due to an applied coating) depends upon the ratio $\beta$ of the sound velocity in the coating to that in the sensor. If the ratio $\beta$ were close to one, the resonant frequency would not change.

Many factors, such as anisotropy, residual stress, temperature, pressure of the environment, and demagnetizing factor have an influence on the actual state of magnetization of the sensor material. Due to the $\Delta E$-effect, this directly affects the resonant frequency. Since the sound velocity of the sensor material can be derived from the resonance frequency, the same state of magnetization has to be restored in order to get reproducible measurements. It has been identified that to achieve this, one can sweep the DC biasing field and measuring the minimal resonant frequency with respect to the bias field before and after deposition of the coating. Suppose a bare sensor element, of which the initial mass $m_0$ and initial resonant frequency $f_0$ are known or measured, is coated with one or more consecutive layers (i=1,2 ... N) of an elastic material while the new masses $m_i'$ and resonant frequencies $f_i'$ after each coated layer are measured. Then the elasticity of the coating/layer can be calculated by curve-fitting the measurement data according to Eqn. 1 identified above. Thus, once more, a value for the modulus of elasticity, $Y_c$, of the thin-film layer can be directly obtained using an apparatus and method of the invention according to the expression:

$$Y_c = \rho_c \cdot 4L^2 f_0^2 \cdot \frac{\sum_{i=1}^{N}\left(\left(\frac{f_i'}{f_0}\right)^2 - \frac{m_0}{m_i'}\right)\left(1 - \frac{m_0}{m_i'}\right)}{\sum_{i=1}^{N}\left(1 - \frac{m_0}{m_i'}\right)^2} \qquad \text{Eqn. 1}$$

Eqn. 1 represents the general case where several thin-film layers from 1, 2, ... N are applied consecutively (i=1,2 ... N) to a base magnetostrictive element. Eqn. 1 is simplified where only one thin-film layer is deposited, thus, i=1 and no summation is necessary. Here, $m_0$ is the initial mass of the base element (without a thin-film layer) and $f_0$ is the base element's resonant frequency measured with no thin-film layer. Once the base element is at least partially coated with one or more thin-film layers, a new mass $m_i'$ and resonant frequency $f_i'$ of the sensor element measured after each coating/layer is applied, are used in the summation of Eqn. 1.

Figure 6:
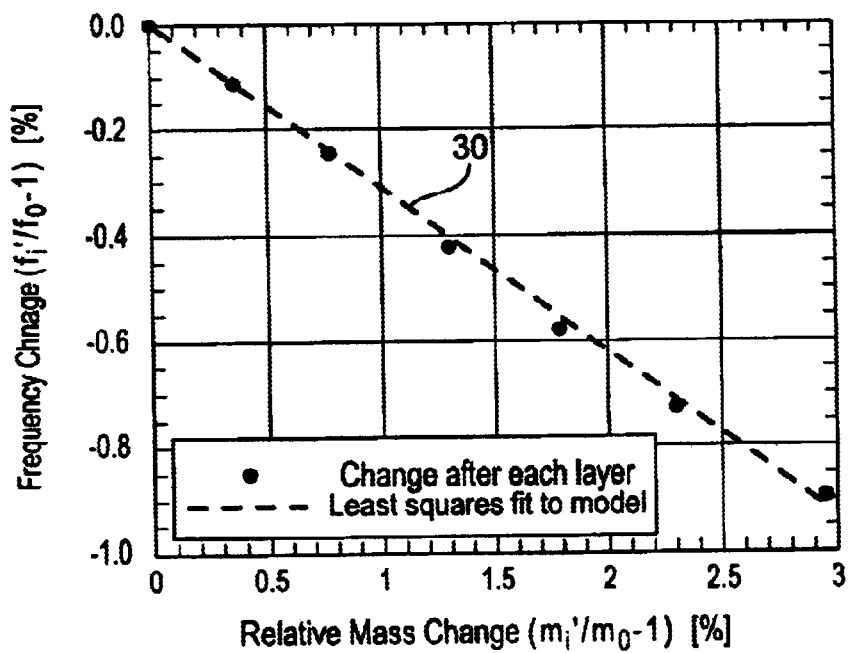
FIG. 6 graphically depicts the relationship between change of resonant frequency identified according to the invention vs. relative mass change as layers of a thin-film, such as silver, were added to a top surface of a base element such as that represented in FIG. 4 made from a METGLAS® 2826 MB ribbon element.
Figure 7:
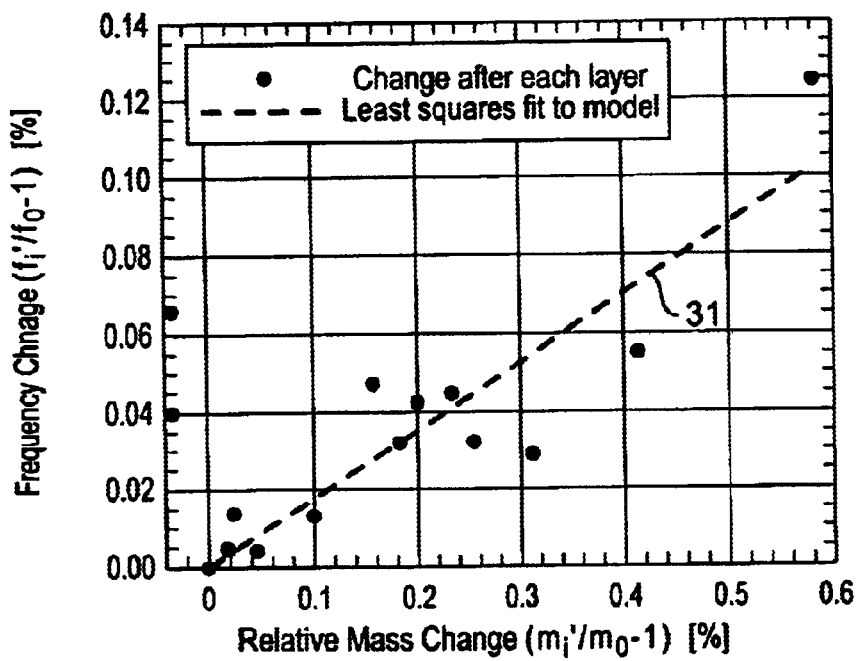
FIG. 7 graphically depicts the relationship between change of resonant frequency identified according to the invention vs. relative mass change as layers of a thin-film, such as aluminum, were added to a top surface of a base element such as that represented in FIG. 4 made from a METGLAS® 2826 MB ($Fe_{40}Ni_{38}Mo_4B_{18}$) ribbon element.

FIG. 6 graphically depicts at 30 the relationship between change of resonant frequency identified according to the invention vs. relative mass change as layers of a thin-film, such as silver, were added to a top surface of a base element such as that represented in FIG. 4 made from a METGLAS® 2826 MB ribbon element. FIG. 7 graphically depicts at 31 the relationship between change of resonant frequency identified according to the invention vs. relative mass change as layers of a thin-film, such as aluminum, were added to a top surface of a base element such as that represented in FIG. 4 made from a METGLAS® 2826 MB ($Fe_{40}Ni_{38}Mo_4B_{18}$) ribbon element.

Figure 8:
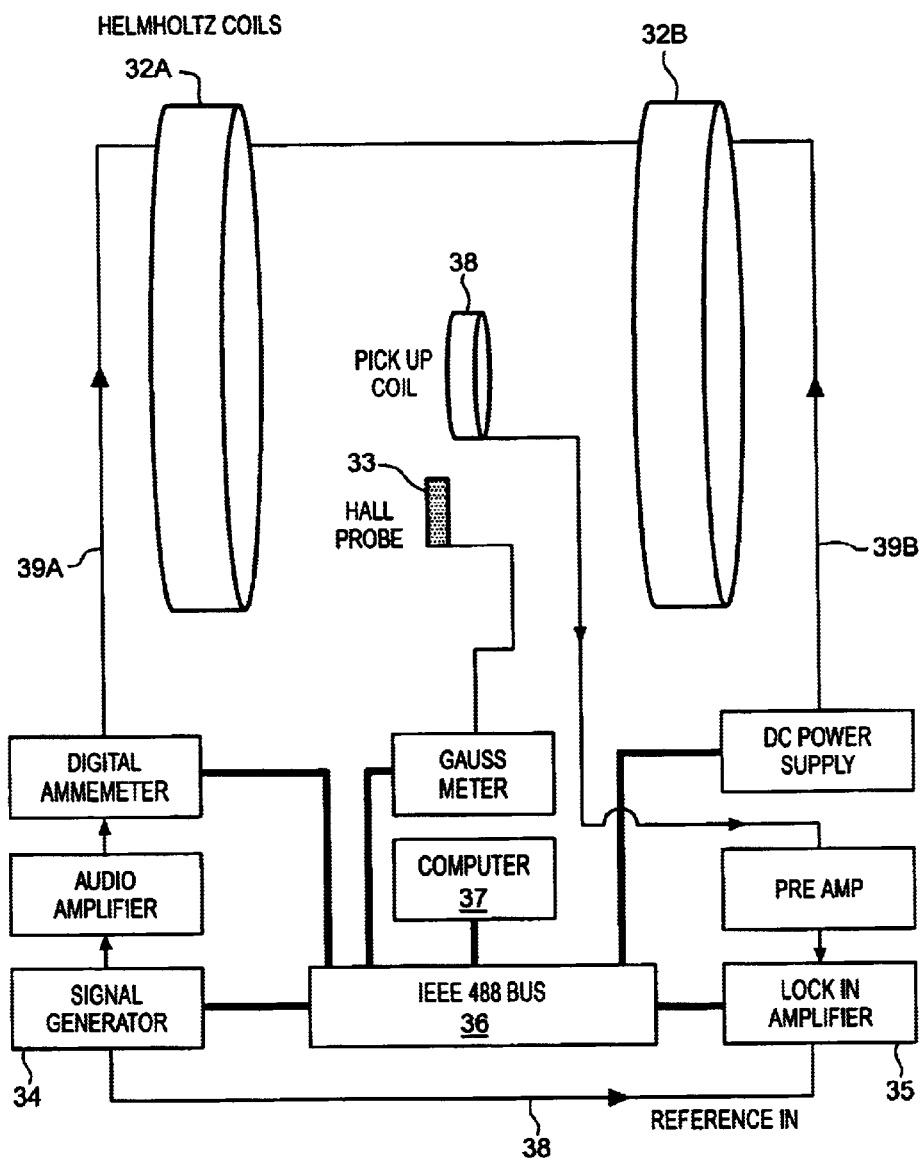
FIG. 8 is a schematic representing further details of an apparatus of the invention, here using a system of Helmholtz coils paired to generate an interrogation field to cause the sensor element (not shown and labeled here, but is positioned therebetween for exposure to the interrogation field) to vibrate and emit energy for receipt by the pick-up coil. A processor incorporated into the unit labeled "computer" can be used to process the sensor information received by the pick-up coil for output in suitable form, by way of screen display, printout, or other visual display device capable of communicating the elasticity characteristics information to a user. Well known graphic user interface devices may be employed here.

FIG. 8 is a schematic representing further details of an apparatus of the invention, here using a system of Helmholtz coils 32A, 32B paired to generate (signal generator labeled, for reference, at 34 as well as lock in amp 35 and reference in 38) an interrogation field by way of electrical communication pathways 39A, 39B to cause the sensor element to vibrate and emit energy for receipt by the pick-up coil 38. Helmholtz coil systems, suitable for use here, include those currently commercially available from Walker Scientific company, product literature can be found and viewed on-line (e.g., www.walkerscientific.com/HelmholtzCoils/) For simplicity in FIG. 8, the sensor element (such as that at 50 in FIG. 10) is not shown and labeled here, but is positioned between coils 32A, 32B for exposure to the interrogation field generated thereby. In the setup of FIG. 8, a probe 33 has been positioned for measuring/monitoring the interrogation field generated (especially for purposes of experimentation). A processor incorporated into the unit labeled computer 37 can be used to process the sensor information received by the pick-up coil 38 for output in suitable form, by way of screen display, printout, or other visual display device capable of communicating the elasticity characteristics information to a user. Well known graphic user interface devices may be employed here.

Figure 9:
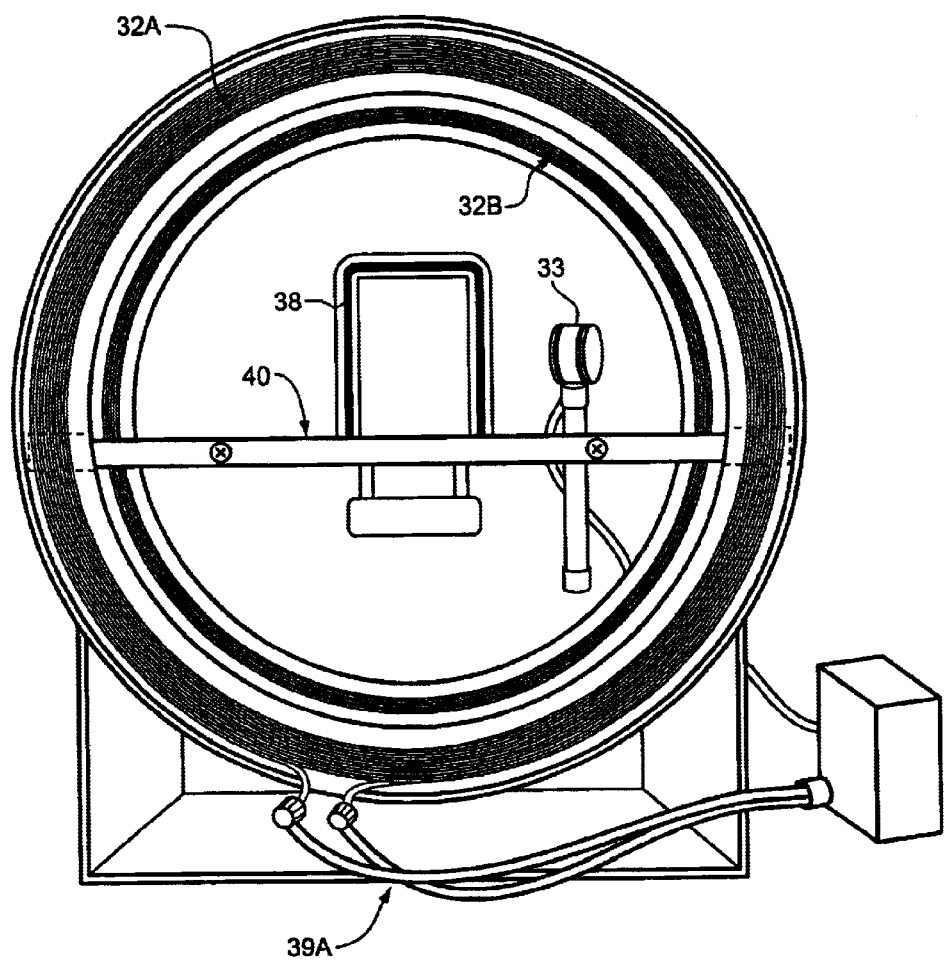
FIG. 9 illustrates an end view looking into the round of the Helmholtz coil pair at the pick-up coil (here, encased in a rectangular configuration) and the Hall probe (for measuring interrogation field for purposes of experimentation.
Figure 10:
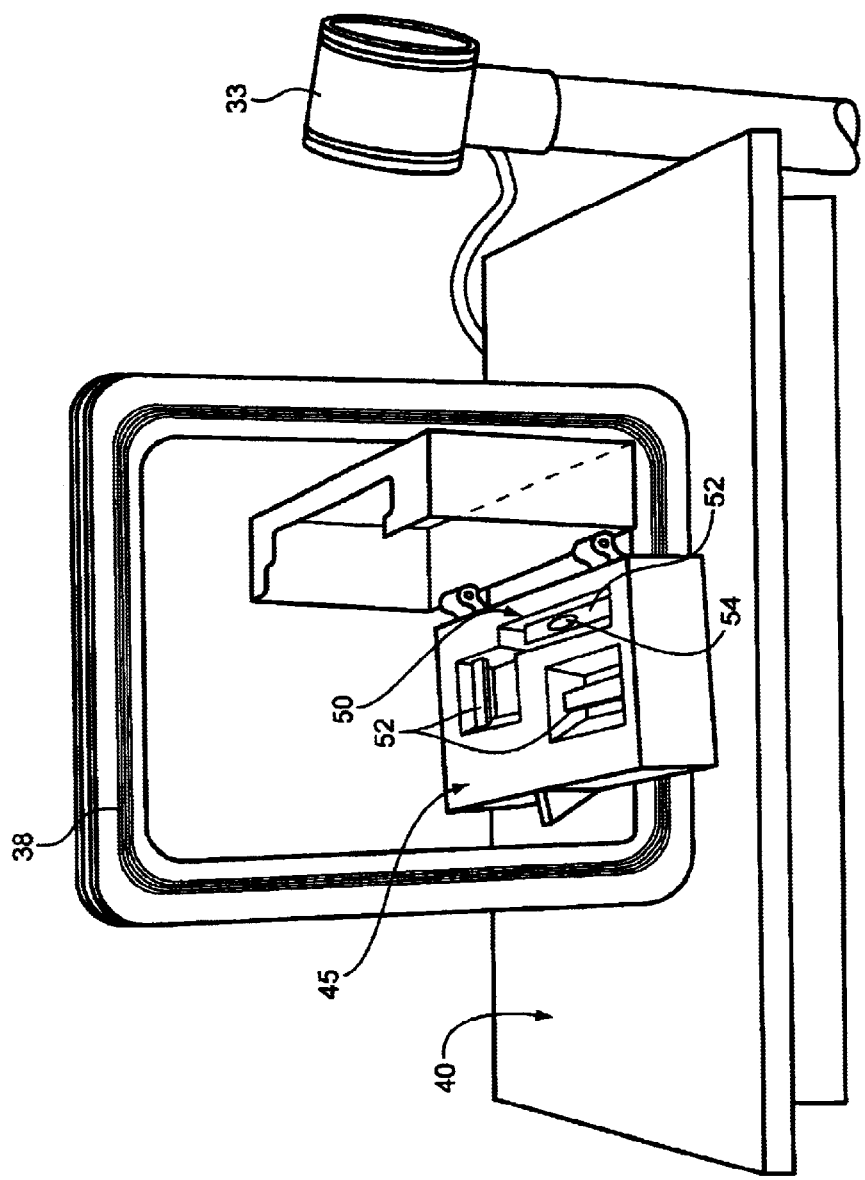
FIG. 10 is an isometric providing a closer-in view of a receptacle disposed within the rectangular-configured pick-up coil. The receptacle is shown holding the sensor element such that elasticity characteristics (for example, a bioactive response curve illustrating coagulation) of a drop of blood deposited atop the base element can be monitored according to the invention.

FIG. 9 illustrates an end view looking into the round of the Helmholtz coil pair of FIG. 8 at the pick-up coil (here, encased in a rectangular configuration also labeled 38) and the Hall probe 33. As can be seen better in the close-up view of FIG. 9 labeled FIG. 10, a receptacle 45 and pick-up coil 38 are collectively supported by a shelf/support-member 40. The receptacle is shown holding the sensor element. The sensor element 50 is comprised of a drop of a bio-substance (such as blood) at 54 deposited on a surface of base element 52. In FIG. 10, for purposes of controlling the environment around the sensor element 50 when elasticity characteristics measurements are taken according to the invention (for example, to produce a bioactive response curve illustrating coagulation), the receptacle 45 has a hinged cover 46. The cover can be positioned over the element 50.

Figure 11:
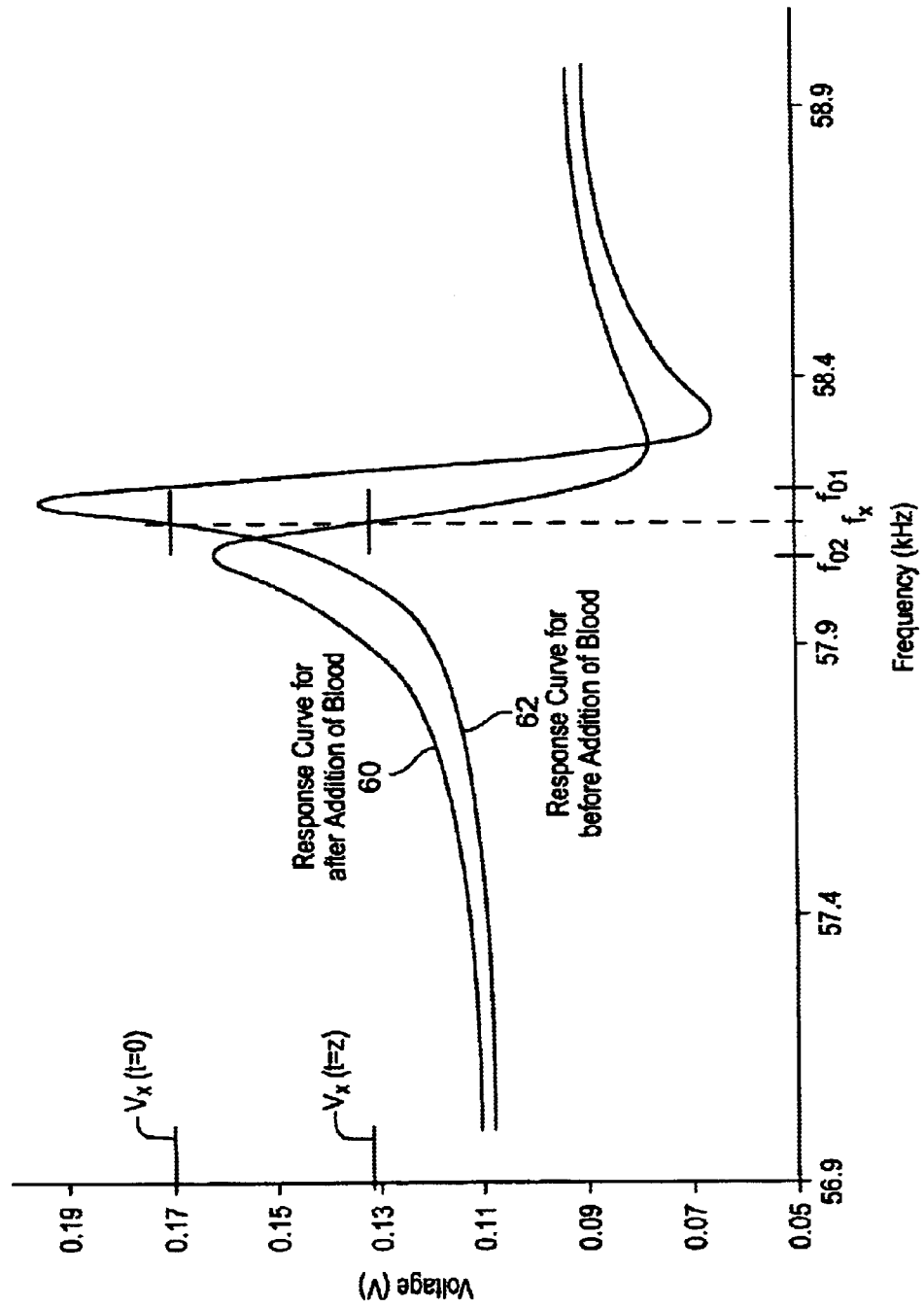
FIG. 11 graphically depicts the shift in resonant frequency from $f_{o1}$ for a base magetostrictive element to $f_{o2}$ for a sensor element (base element with layer, here by way of example, 4 μL of blood)—resonant frequency shifts to left due to addition of mass. Also identified is $f_x$, a frequency selected along a steep section of the initial curve of the base element. In producing a bioactive reaction curve (such as a coagulation response curve) according to the invention, one might select $f_x$, $f_{o2}$, or $f_{o1}$ for monitoring emissions from the sensor element (base element with thin-film layer) over a time interval, Δt, such that emission measurements are obtained and plotted for at least from time t=0 to t=z.
Figure 12:
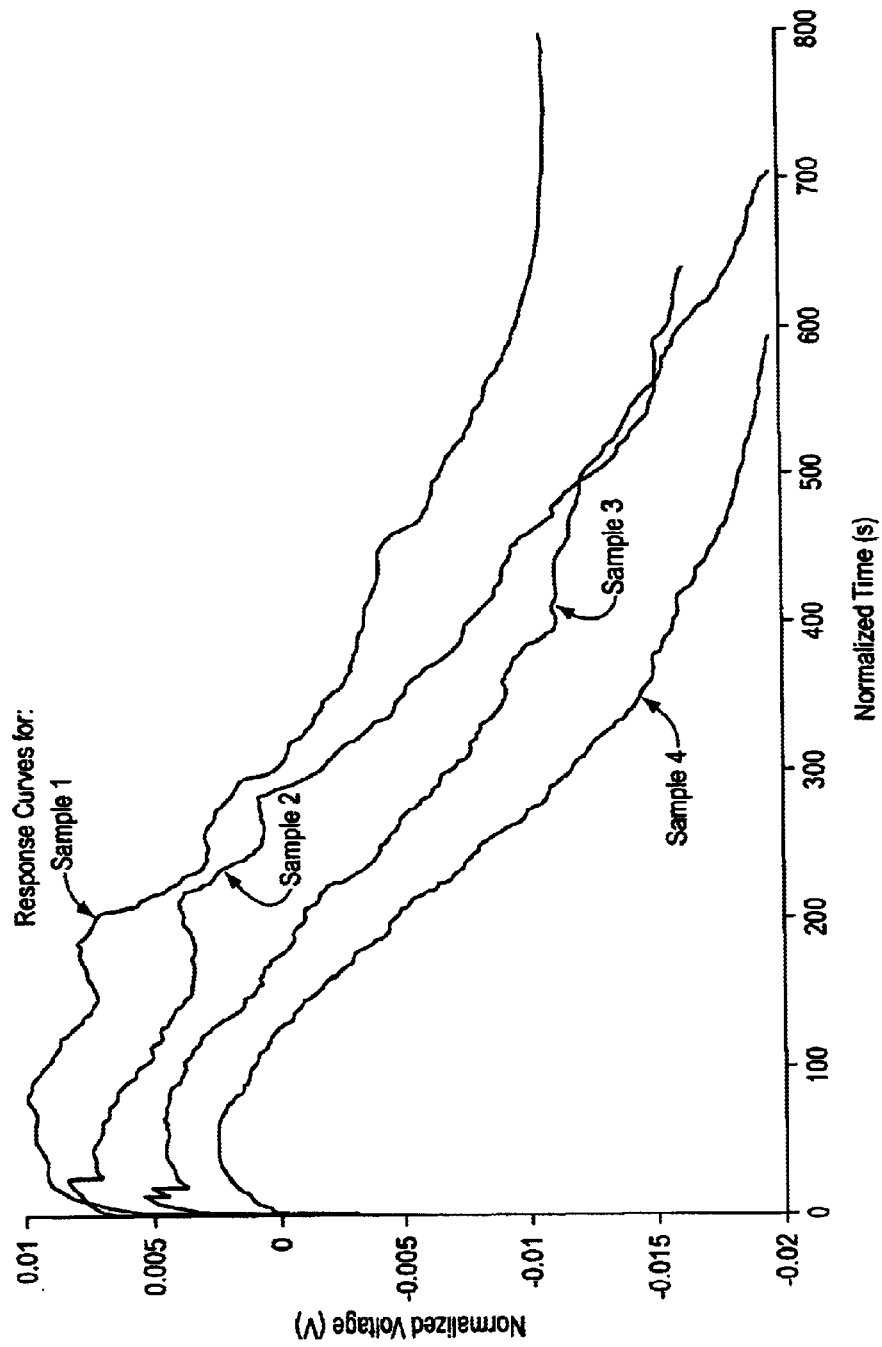
FIG. 12 graphically depicts bioactive response curves for four samples of blood (here, by way of example, taken from a rat) to illustrate that comparisons may be made of blood from different animals according to the invention.

FIG. 11 graphically depicts the shift in resonant frequency from $f_{o1}$ for a base magetostrictive element (curve 62) to $f_{o2}$ for a sensor element (base element with layer, here by way of example, 4 μL of blood, labeled curve 60)—resonant frequency shifts to left due to addition of mass. As shown, selection of a frequency, here identified as $f_x$, along the steep downward sloping portion of curve 62 (where voltage is changing rapidly for a given frequency) is done (Point X). At the selected frequency, $f_x$, the reaction kinetics of the loaded sensing element unit is observed. By monitoring at the selected frequency, $f_x$, the voltage change over time at that frequency can be tracked. As surface viscosity changes (e.g., blood coagulates) the voltage response profile gives valuable information concerning the coagulation process. In producing a bioactive reaction curve (such as a coagulation response curve) according to the invention, one might select $f_x$, $f_{o2}$, or $f_{o1}$ for monitoring emissions from the sensor element (base element with thin-film layer) over a time interval, Δt, such that emission measurements are obtained and plotted for at least from time t=0 to t=z. For example, if $f_x$ is selected, one could observe the change in voltage from $V_x(t=0)$ to $V_x(t=z)$ to produce curves such as the various profiles illustrated by way of example in FIGS. 12–16, wherein the change in voltage measured by sensing emissions of the sensor element over time is plotted to visually track the coagulation process of a thin-film layer (which, in FIGS. 12–16 is blood of various mammals).

Figure 13:
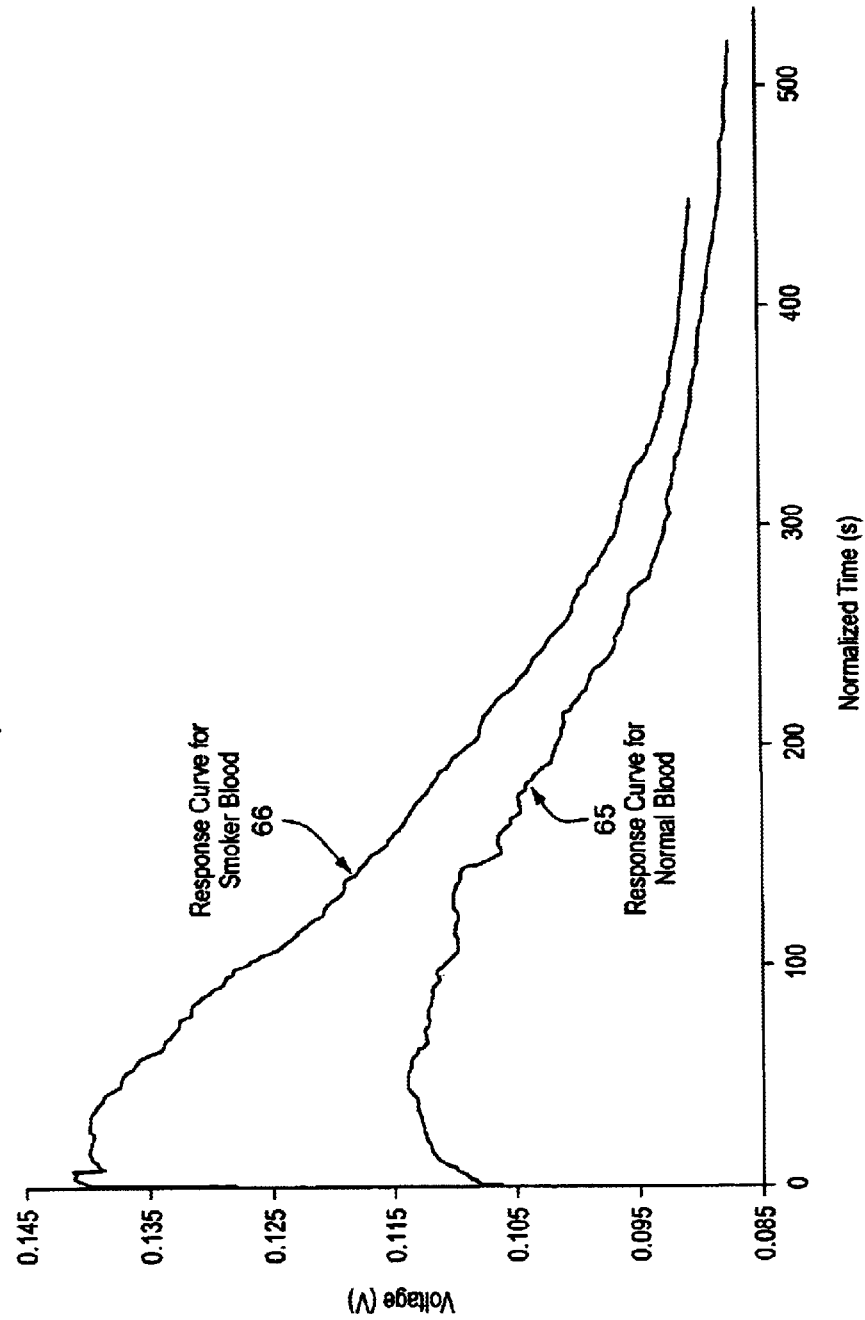
FIG. 13 graphically depicts bioactive response curves for two samples of human blood, one taken from a subject that does not smoke and another for a subject that does.
Figure 14:
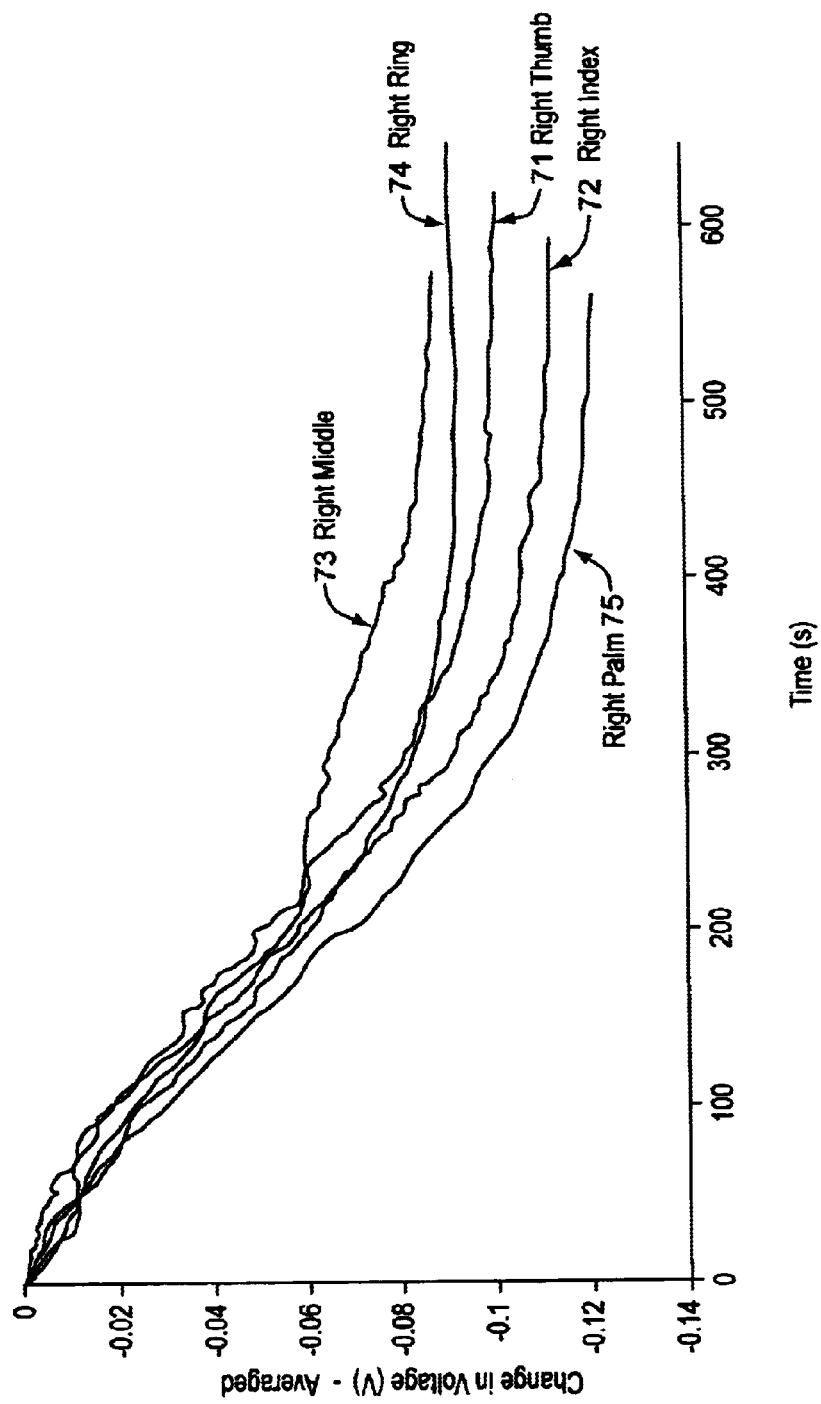
FIG. 14 graphically depicts bioactive response curves for four samples of blood (here, by way of example, taken from different fingers from a human subject) to illustrate comparison and repeatability of the technique of the invention.

Returning to FIG. 12, bioactive response curves for four samples of blood (here, by way of example, taken from a rat) are illustrated. One can see that comparisons may be made of blood from different animals according to the invention. FIG. 13 graphically depicts bioactive response curves for two samples of human blood, one taken from a subject that does not smoke (curve labeled 655) and another for a subject that does (curve labeled 66). FIG. 14 graphically depicts bioactive response curves for four samples of blood (here, by way of example, taken from different fingers from a human subject-the curves labeled consecutively as 71–75 for reference) to illustrate comparison and repeatability of the technique of the invention.

Figure 15:
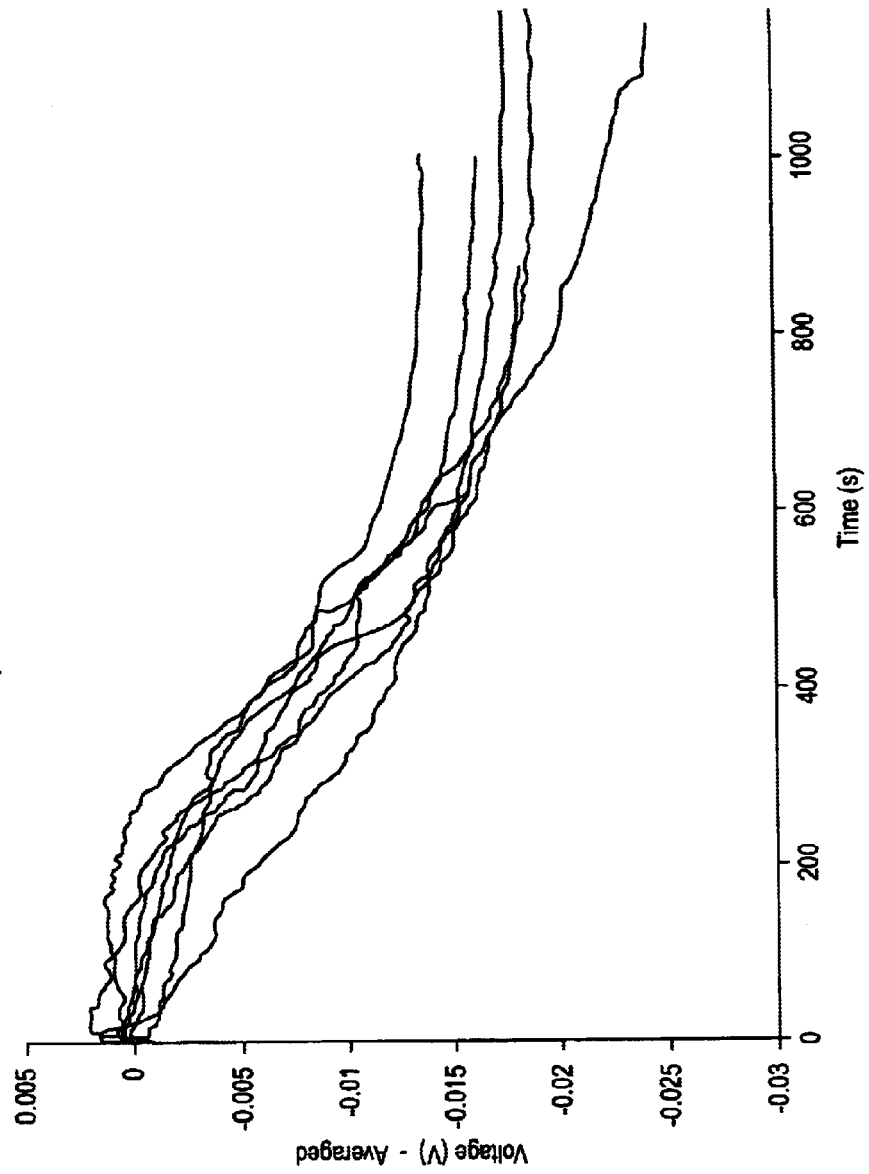
FIG. 15 graphically depicts bioactive response curves for four samples of blood (here, by way of example, taken from several different horses) to illustrate that comparisons may be made of blood from different animals according to the invention.
Figure 16:
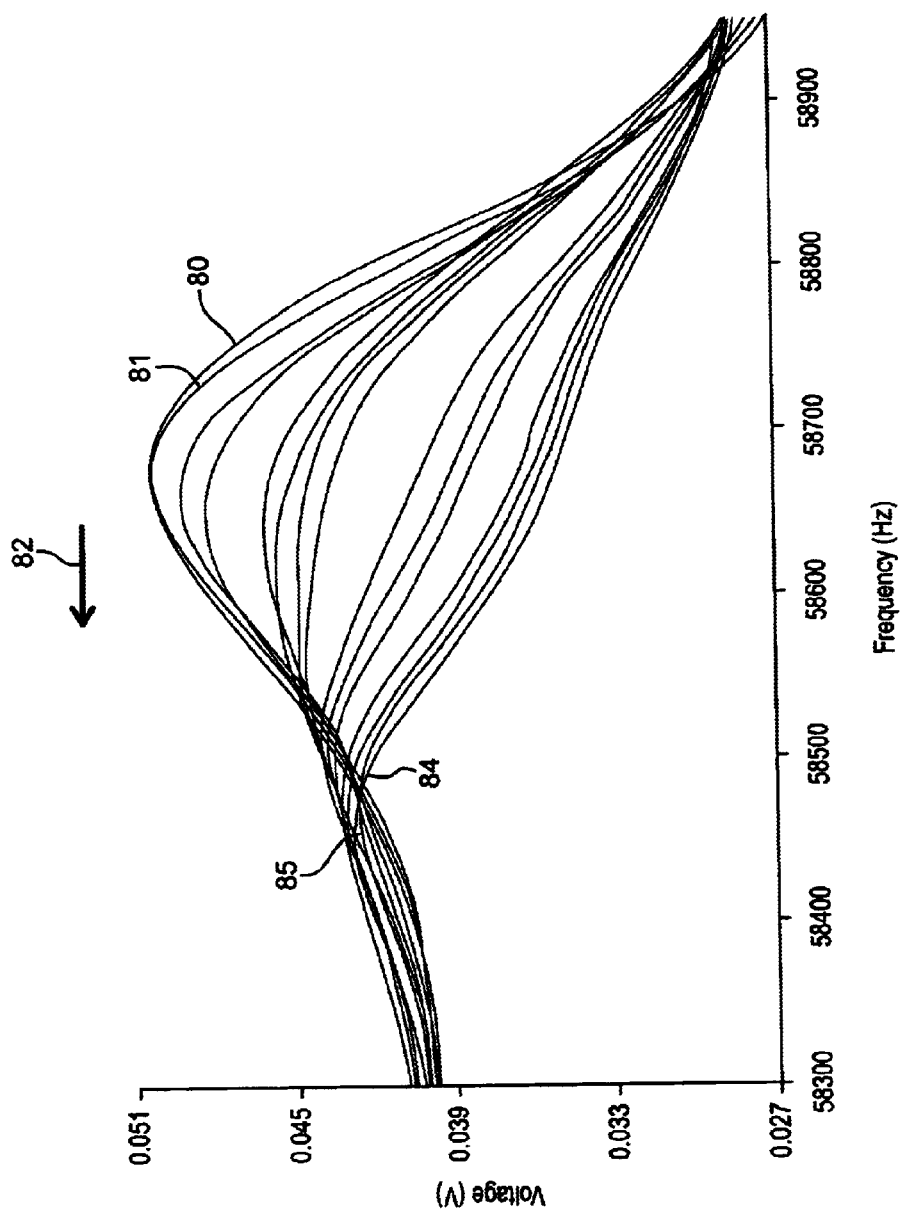
FIG. 16 graphically depicts several curves illustrating the change in frequency response as human blood (taken from one subject) coagulates. As the blood bio-layer starts coagulating (whereby its viscosity changes with time) the resonant frequency peak continues to shift downwardly and to the left as illustrated.

FIG. 15 graphically depicts bioactive response curves for four samples of blood (here, by way of example, taken from several different horses) to illustrate that comparisons may be made of blood from different animals according to the invention. FIG. 16 graphically depicts several curves, two of the curves in the top right-hand region of the graph are labeled 80 and 81 and two 'undermost' curves peaking between 58400 Hz and 58500 Hz are labeled 84 and 85, illustrating the change in frequency response as human blood (taken from one subject) coagulates. As the blood bio-layer starts coagulating (whereby its viscosity changes with time) the resonant frequency peak continues to shift downwardly and to the left in the direction labeled with arrow 82 as illustrated.

Figure 17:
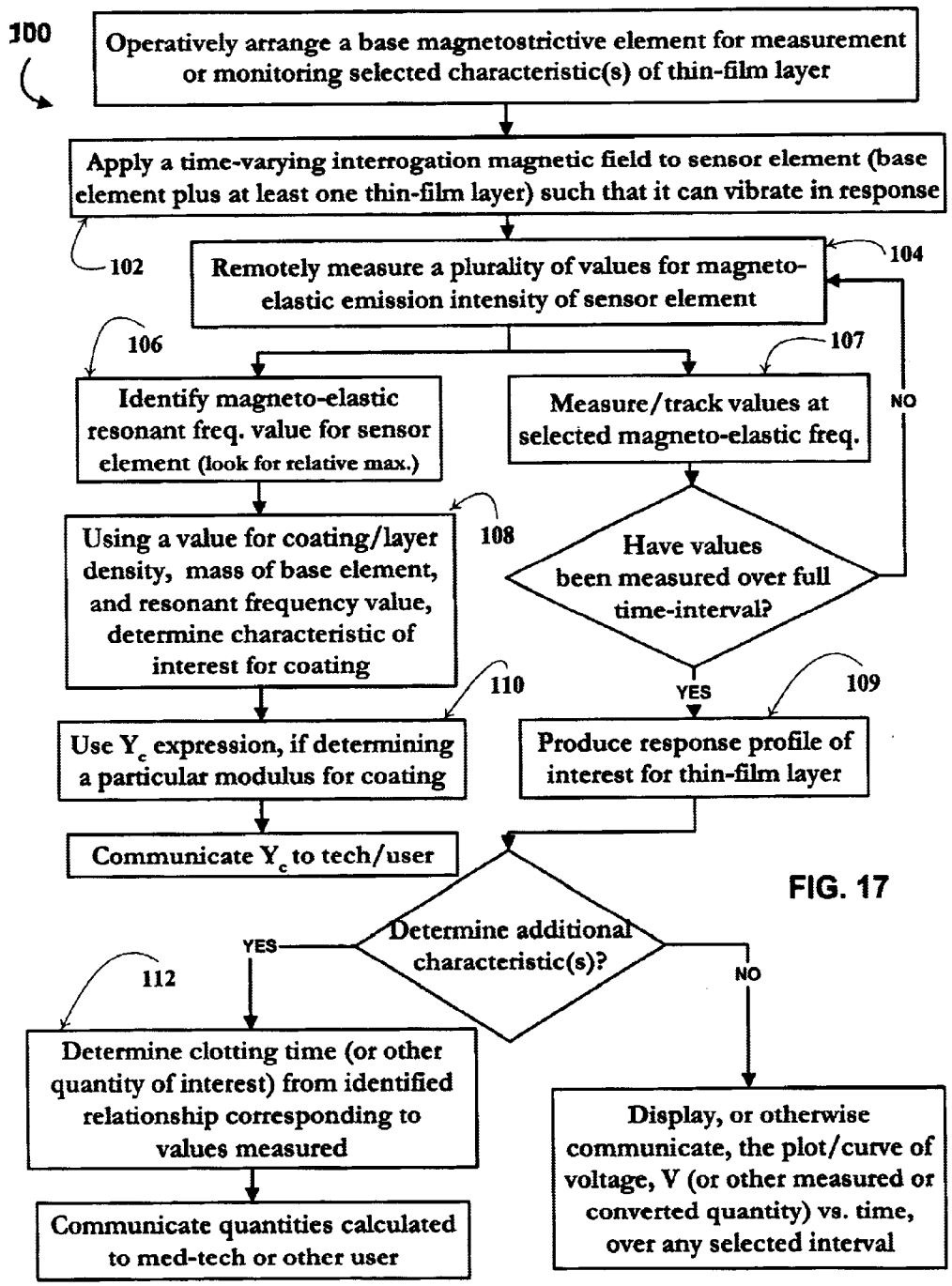
FIG. 17 is a flow diagram depicting features of a method 100 of the invention including details of further distinguishing features thereof.

Finally, FIG. 17 illustrates, in flow diagram format, details of the further distinguishing features of a method 100 for determining elasticity characteristics of a thin-film layer at least partially coating a surface of a base magnetostrictive element. Certain of the features depicted in FIG. 17 have been labeled and referenced earlier. This diagram aids in understanding operation of the apparatus as well as in appreciating the novel features of a method of the invention and is readily understood by following the detailed explanation in each box shown in flow-diagram format.

From a frequency response curve produced for a sensing element with blood, one might select a frequency at which voltage is changing rapidly: For example, one might choose a point on FIG. 11 at $f_x$ in the steep downwardly sloping portion of curve 62, to the left of the point at which a relative maximum voltage reading occurs—this relative max. corresponding with the characteristic resonant frequency of the sensor structure. At the preselected frequency, the magnetoelastic emissions from a sensor element to which a drop of blood has been placed (sometimes 'loaded' sensing element) are measured over a selected period of time, Δt (ranging from several seconds to several minutes), while the blood coagulates. In this manner, data collected over Δt may be used to create a response profile to characterize the blood sample: For example, emission intensity measured over Δt as voltage readings using a suitable pick-up coil system, allows one to construct rresponse profiles such as those shown in FIGS. 12–16 (V vs. time). Alternatively, by measuring magnetoelastic emissions from a sensing element (base element plus coating/layer) over Δt, and tracking the change in characteristic resonant frequency $f_0$ (or a harmonic, $f_n$, thereof) by, for example, converting relative maximum emission values measured by the pick-up coil into resonant frequency values, a frequency-response profile can be created ($f_n$ vs. time) for the sensing element against which later blood-samples taken and measured can be compared, for clinical purposes.

According to one aspect of the method described above to characterize using resonant frequency data of an unknown coating/layer atop a magnetoelastic sensing element, one can use the apparatus of the invention to measure coagulation of blood/bioactive coagulation reactions in the following manner. First, the characteristic resonant frequency for a loaded sensing element of selected material and dimensions (for example, in a strip/ribbon shape of METGLAS® amorphous alloy) is identified, $f_0$ in the curve above. As the blood/solution coagulates at the strip surface the resultant change in surface characteristics/viscosity will result in a change in the sensing unit's resonant frequency. This can be shown graphically, later-in-time, as a shift along the X-axis to the left of the frequency response curve (see FIG. 11 graphically representing the shift to the left of the base magetostrictive element to which a thin-film layer has been added). By way of further example, FIG. 16 graphically illustrates the shift to the left in frequency response over time of a sensing element to which blood has been added; as one can see, the resonant frequency peak decreases and shifts go the left as the blood coagulates.

By way of example only: For 500 nm thick films, the measured Young's modulus of elasticity for Al and Ag was found according to the invention, to be within 1.6% of standard data; and the elasticity of coatings approximately 30 nm thick were handily measured. In the event a "package" of different types of sensing information about one environment is sought, more than one sensor may be maintained in an ordered array, for example, by being organized to extend along or contained within chambers of a support member. Each sensor within the array may have a distinct operating range, allowing the receiver to distinguish emissions received from each separate sensor. Thus, the separate types of sensing information can be obtained, tracked and computed.

While certain representative embodiments and details have been shown merely for the purpose of illustrating the invention, those skilled in the art will readily appreciate that various modifications may be made to these representative embodiments without departing from the novel teachings or scope of this invention. Accordingly, all such modifications are intended to be included within the scope of this invention as defined in any illustrative-claim included below. Although the commonly employed preamble phrase "comprising the steps of" may be used herein, or hereafter, in a method claim, the Applicants in no way intend to invoke 35 U.S.C. Section 112 §6. Furthermore, in any claim that is filed hereafter (as well as any claim included herewith for illustrative purposes), any means-plus-function clauses used, or later found to be present, are intended to cover the structures described herein as performing the recited function and not only structural equivalents but also equivalent structures.

What is claimed is:

1. An apparatus for determining viscosity characteristics of a thin-film layer, comprising:
    a sensor element having a base magnetostrictive element at least one surface of which is at least partially coated with the thin-film layer, said sensor element operatively arranged to vibrate within a time-varying interrogation magnetic field;
    a receiver, remote from said sensor element, to measure a plurality of values for magneto-elastic emission intensity of said sensor element to identify a magneto-elastic resonant frequency value for said sensor element; and
    a processor adapted for determining at least one of the viscosity characteristics using a value for density of the thin-film layer and a value for mass of said base magnetostrictive element and said magneto-elastic resonant frequency value.

2. The apparatus of claim 1 wherein said magneto-elastic resonant frequency value corresponds with a relative maximum of said plurality of values for magneto-elastic emission intensity measured; the viscosity characteristics comprise a response profile plotted against time over a response-time interval for the thin-film layer; and said base magnetostrictive element is made of an alloy of an element selected from the group consisting of iron, cobalt, samarium, yttrium, gadolinium, terbium, and dysprosium.

3. The apparatus of claim 1 wherein said magneto-elastic emission is an electromagnetic emission, said receiver comprises an electromagnetic pick-up coil, said magnetostrictive element is elongated in shape, and the thin-film layer comprises a fluent bio-substance.

4. The apparatus of claim 1 wherein said magneto-elastic emission is an acoustic emission, and said receiver comprises an electroacoustic device containing a transducer for operation over a range of frequencies from 1 KHz to 1 GHz, and said magneto-elastic resonant frequency value is an acoustic resonant frequency value, and the thin-film layer comprises a thin film deposit.

5. The apparatus of claim 3 wherein a thickness, $t_f$, of the thin-film layer is less than a thickness, $t_{mag}$, of said base magnetoelastic element and a length, 1, of said sensor element is at least twice a width, w, thereof.

6. The apparatus of claim 1 wherein the thin-film layer comprises a fluent bio-substance deposited atop said at least one surface, said fluent bio-substance comprises a biologic agent, and the viscosity characteristics comprise at least one value for said biologic agent, taken over a response-time interval.

7. The apparatus of claim 1 wherein the said magnetostrictive element is a micro-element made of a ferrous alloy; and further comprising a processor for determining the viscosity characteristics which comprises a modulus value, $Y_c$, for the thin-film layer, according to the expression:

$$Y_c = \rho_c \cdot 4L^2 f_0^2 \cdot \frac{\left(\left(\frac{f'}{f_0}\right)^2 - \frac{m_0}{m'}\right)}{\left(1 - \frac{m_0}{m'}\right)^2}$$

wherein $p_c$ denotes density of the thin-film layer, L denotes a length of said magnetostrictive element, $m_c$ denotes a mass of said magnetostrictive element, $f_o$ is a resonant frequency of said magnetostrictive element, m'denotes a mass of said sensor element, and f denotes a resonant frequency of said sensor element.

8. The apparatus of claim 1 wherein said receiver comprises an electromagnetic pick-up coil, said time-varying interrogation magnetic field comprises a pulse, said magneto-elastic emission is an electromagnetic emission, said magnetostrictive element is ribbon shaped and made of an alloy.

9. The apparatus of claim 1 wherein said receiver comprises an electromagnetic pick-up coil, and further comprising:

- a processor for determining the viscosity characteristics;
- a field generating coil, remote from said receiver pick-up coil, for generating said time-varying interrogation magnetic field; and
- a receptacle for accepting said sensor element when so determining.

10. An apparatus for determining viscosity characteristics of a thin-film layer of a fluent bio-substance, comprising:

- a sensor element having a base magnetostrictive element at least one surface of which is at least partially coated with the thin-film layer, said sensor element operatively arranged to vibrate within a time-varying interrogation magnetic field;
- a receiver, remote from said sensor element, to measure a plurality of successive values for magneto-elastic emission intensity of said sensor element at a preselected magneto-elastic frequency; and
- a processor adapted for producing a response profile, using said values for emission intensity, for the bio-substance.

11. The apparatus of claim 10 wherein an identified magneto-elastic resonant frequency value for said sensor element is used to identify said preselected magneto-elastic frequency, said measure of said plurality occurs over a response-time interval, and said response profile comprises a coagulation reaction curve for the bio-substance.

12. The apparatus of claim 10 further comprising a receptacle for accepting said base magnetostrictive element such that said element has at least one free-end; and wherein:

the fluent bio-substance comprises a drop of blood;

said blood is deposited atop said at least one surface nearby said free-end; and said processor further adapted for determining, using said response profile, a blood clotting time.

13. The apparatus of claim 10 wherein: said receiver comprises an electromagnetic pick-up coil; the fluent bio-substance comprises a biologic agent and-bleed; and said response profile comprises a bioactive reaction response curve for the bio-substance.

14. The apparatus of claim 10 wherein said receiver comprises an electromagnetic pick-up coil, and further comprising:

said preselected magneto-elastic frequency is a resonant frequency value for said sensor element;

a field generating coil, remote from said receiver pick-up coil, for generating said time-varying interrogation magnetic field; and a receptacle for accepting said sensor element when so producing.

15. The apparatus of claim 10 wherein said response profile comprises a coagulation reaction curve represented by a plurality of successive voltage values respectively associated with said plurality of successive values for magneto-elastic emission intensity measured, plotted against time over a selected response-time interval.

16. A method for determining viscosity characteristics of a thin-film layer at least partially coating a surface of a base magnetostrictive element, comprising the steps of:

applying a time-varying interrogation magnetic field to a sensor element comprising the base magnetostrictive element and thin-film layer, operatively arranged to vibrate in response to said interrogation magnetic field;

remotely measuring a plurality of values for magneto-elastic emission intensity of said sensor element to identify a magneto-elastic resonant frequency value therefor; and using a value for density of the thin-film layer and a value for mass of the base magnetostrictive element and said magneto-elastic resonant frequency value, determining at least one of the viscosity characteristics.

17. The method of claim 16 wherein: said emission comprises an electromagnetic emission; said step of remotely measuring comprises receiving with a remote receiver comprising a pick-up coil; and said step of determining the viscosity characteristic comprises producing a response profile comprising values plotted against time over a response-time interval for the thin-film layer comprising a thin film deposit.

18. The method of claim 16 wherein said operatively arranging comprises arranging said sensor element within a receptacle; and step of determining the elasticity characteristic comprises finding at least one modulus value for the thin-film layer taken over a response-time interval during which the thin-film layer is drying, said thin-film layer comprises a coating selected from the group consisting of a polymeric coating, a coating of paint, and a coating of an adhesive.

19. The method of claim 16 wherein said step of determining the viscosity characteristic comprises finding a modulus value, $Y_c$, for the thin-film layer, according to the expression:

$$Y_c = \rho_c \cdot 4L^2 f_0^2 \cdot \frac{\left(\left(\frac{f'}{f_0}\right)^2 - \frac{m_0}{m_i'}\right)}{\left(1 - \frac{m_0}{m'}\right)^2}$$

wherein $p_c$ denotes density of the thin-film layer, L denotes a length of said magnetostrictive element, $m_0$ denotes a mass of said magnetostrictive element, $f_0$ is a resonant frequency of said magnetostrictive element, $m'$ denotes a mass of said sensor element, and $f'$ denotes a resonant frequency-of said sensor element.

20. A method for determining viscosity characteristics of a thin-film layer of a fluent bio-substance at least partially coating a surface of a base magnetostrictive element, comprising the steps of:

applying a time-varying interrogation magnetic field to a sensor element comprising the base magnetostrictive element and thin-film layer, operatively arranged to vibrate in response to said interrogation magnetic field;

remotely measuring, over a response-time interval, a plurality of successive values for magneto-elastic emission intensity of said sensor element at a preselected magneto-elastic frequency; and using said values for emission intensity, producing an-- elasticity a response profile for the bio-substance.

21. The method of claim 20 wherein: said emission comprises an electromagnetic emission; said step of remotely measuring comprises receiving with a pick-up coil not in direct electrical connection with said sensor element; said step of remotely measuring further comprises using a magneto-elastic resonant frequency value identified for said sensor element to identify said preselected magneto-elastic frequency; and said response profile comprises a coagulation reaction curve for the bio-substance.

22. The method of claim 20 wherein: said emission comprises an acoustic emission; said step of remotely measuring comprises receiving with an electroacoustic device containing a transducer not in direct electrical connection with said sensor element; said step of producing said response profile comprises displaying a bioactive reaction response curve for the bio-substance.

23. The method of claim 20 wherein said step of producing said response profile comprises representing a coagulation reaction curve by plotting a plurality of successive voltage values respectively associated with said plurality of successive values for magneto-elastic emission intensity measured, against time over a selected response-time interval.

24. The method of claim 20 wherein said sensor element is arranged within a receptacle such that said element has at least one free-end; and said step of using said values for emission intensity further comprises determining a blood clotting time; and further comprising the step of depositing the fluent big-substance atop said surface nearby said free-end.

* * * * *